(12) United States Patent
Krieger et al.

(10) Patent No.: US 11,406,495 B2
(45) Date of Patent: Aug. 9, 2022

(54) EXPANDABLE SUPPORT FRAME AND MEDICAL DEVICE

(71) Applicant: Cook Medical Technologies LLC, Bloomington, IN (US)

(72) Inventors: Joshua Krieger, Bloomington, IN (US); Sean Chambers, Bloomington, IN (US); Zachary Berwick, Indianapolis, IN (US); Ghassan Kassab, Zionsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 313 days.

(21) Appl. No.: 15/804,049

(22) Filed: Nov. 6, 2017

(65) Prior Publication Data
US 2018/0055635 A1     Mar. 1, 2018

Related U.S. Application Data

(63) Continuation of application No. 14/176,364, filed on Feb. 10, 2014, now abandoned.

(60) Provisional application No. 61/763,107, filed on Feb. 11, 2013.

(51) Int. Cl.
*A61F 2/24*     (2006.01)

(52) U.S. Cl.
CPC .... *A61F 2/2418* (2013.01); *A61F 2220/0016* (2013.01); *A61F 2220/0058* (2013.01)

(58) Field of Classification Search
CPC ........................................................ A61F 2/24
See application file for complete search history.

(56) References Cited

U.S. PATENT DOCUMENTS

| 3,012,882 | A | 12/1961 | Muldawer et al. |
| 3,014,104 | A | 12/1961 | Cobine et al. |
| 3,174,851 | A | 12/1961 | Buehler et al. |
| 3,063,967 | A | 11/1962 | Schultz |
| 3,169,945 | A | 2/1965 | Hostettler et al. |
| 3,391,126 | A | 7/1968 | Baggett et al. |
| 3,464,065 | A | 9/1969 | Cromie |

(Continued)

FOREIGN PATENT DOCUMENTS

| AU | 2003265468 | 8/2002 |
| AU | 2002248669 | 10/2002 |

(Continued)

OTHER PUBLICATIONS

Kinney, T.E., et al., "Acute, reversible tricuspid insufficiency: creation in canine model," Am. J. Physiol. Heart Circ. Physiol. 260: H638-H641, 1991.

(Continued)

*Primary Examiner* — Jacqueline Woznicki
(74) *Attorney, Agent, or Firm* — MacMillan, Sobanski & Todd, LLC

(57) ABSTRACT

Support frames and medical devices are described. An example medical device comprises an expandable support frame with first and second leaflets attached to the support frame. Each of the first and second leaflets defines a domed radius that is equal to or less than the radius of the expandable support frame when the expandable support frame is in an expanded configuration and the leaflets are subjected to fluid pressure sufficient to affect closure of the valve orifice.

20 Claims, 5 Drawing Sheets

(56) References Cited

U.S. PATENT DOCUMENTS

| | | |
|---|---|---|
| 3,583,391 A | 6/1971 | Cox et al. |
| 3,589,392 A | 6/1971 | Meyer |
| 3,645,941 A | 2/1972 | Snapp et al. |
| 3,710,744 A | 1/1973 | Goodenough et al. |
| 3,736,598 A | 6/1973 | Bellhouse et al. |
| 3,737,919 A | 6/1973 | Child |
| 3,772,137 A | 11/1973 | Tolliver |
| 3,912,692 A | 10/1975 | Casey et al. |
| 3,942,532 A | 3/1976 | Hunter et al. |
| 3,953,566 A | 4/1976 | Gore |
| 3,983,581 A | 10/1976 | Angell et al. |
| 4,052,988 A | 10/1977 | Doddi et al. |
| 4,076,807 A | 2/1978 | Trinh et al. |
| 4,093,061 A | 6/1978 | Horak |
| 4,106,129 A | 8/1978 | Carpentier et al. |
| 4,218,782 A | 8/1980 | Rygg |
| 4,222,126 A | 9/1980 | Boretos et al. |
| 4,243,775 A | 1/1981 | Rosensaft et al. |
| 4,274,292 A | 1/1981 | Angell |
| 4,272,854 A | 6/1981 | Bokros |
| 4,275,469 A | 6/1981 | Gabbay |
| 4,297,749 A | 11/1981 | Davis et al. |
| 4,300,565 A | 11/1981 | Rosensaft et al. |
| 4,328,592 A | 5/1982 | Klawitter |
| 4,340,977 A | 7/1982 | Brownlee et al. |
| 4,345,340 A | 8/1982 | Rosen |
| 4,350,492 A | 9/1982 | Wright et al. |
| 4,364,126 A | 12/1982 | Rosen |
| 4,429,080 A | 1/1984 | Casey et al. |
| 4,440,789 A | 4/1984 | Mattei et al. |
| 4,441,216 A | 4/1984 | Ionescu et al. |
| 4,470,157 A | 9/1984 | Love |
| 4,494,531 A | 1/1985 | Gianturco |
| 4,506,394 A | 3/1985 | Bedard |
| 4,535,483 A | 8/1985 | Klawitter et al. |
| 4,549,921 A | 10/1985 | Wolfe, Jr. |
| 4,559,945 A | 12/1985 | Koelmel et al. |
| 4,564,014 A | 1/1986 | Fogarty |
| 4,580,568 A | 4/1986 | Gianturco |
| 4,591,630 A | 5/1986 | Gertzman et al. |
| 4,605,730 A | 8/1986 | Shalaby et al. |
| 4,624,256 A | 11/1986 | Messier et al. |
| 4,643,732 A | 2/1987 | Pietsch et al. |
| 4,643,734 A | 2/1987 | Lin |
| 4,653,497 A | 3/1987 | Bezwada et al. |
| 4,657,024 A | 4/1987 | Coneys |
| 4,661,300 A | 4/1987 | Daugherty |
| 4,665,906 A | 5/1987 | Jervis |
| 4,665,918 A | 5/1987 | Garza et al. |
| 4,666,442 A | 5/1987 | Arru et al. |
| 4,675,361 A | 6/1987 | Ward et al. |
| 4,692,164 A | 9/1987 | Dzemeshkevich |
| 4,700,704 A | 10/1987 | Jamiolkowski et al. |
| 4,731,074 A | 3/1988 | Rousseau et al. |
| 4,731,075 A | 3/1988 | Gallo Mezo et al. |
| 4,755,593 A | 7/1988 | Lauren |
| 4,759,758 A | 7/1988 | Gabbay |
| 4,762,129 A | 8/1988 | Bonzel |
| 4,776,337 A | 10/1988 | Palmaz |
| 4,787,901 A | 11/1988 | Baykut |
| 4,788,979 A | 12/1988 | Jarrett et al. |
| 4,791,929 A | 12/1988 | Jarrett et al. |
| 4,798,611 A | 1/1989 | Freeman |
| 4,800,603 A | 1/1989 | Jaffe |
| 4,806,595 A | 2/1989 | Noishiki et al. |
| 4,816,028 A | 3/1989 | Kapadia |
| 4,816,029 A | 3/1989 | Penny et al. |
| 4,832,055 A | 5/1989 | Palestrant |
| 4,836,204 A | 6/1989 | Landymore et al. |
| 4,838,267 A | 6/1989 | Jamiolkowski et al. |
| 4,851,000 A | 7/1989 | Gupta |
| 4,856,510 A | 8/1989 | Kowalewski |
| 4,856,516 A | 8/1989 | Hillstead |
| 4,861,830 A | 8/1989 | Ward et al. |
| 4,872,875 A | 10/1989 | Hwang |
| 4,893,623 A | 1/1990 | Rosenbluth |
| 4,902,508 A | 2/1990 | Badylak et al. |
| 4,911,163 A | 3/1990 | Fina |
| 4,917,089 A | 4/1990 | Sideris |
| 4,923,465 A | 5/1990 | Knock et al. |
| 4,952,215 A | 8/1990 | Ouriel et al. |
| 4,956,178 A | 9/1990 | Badylak et al. |
| 4,969,458 A | 11/1990 | Wiktor |
| 4,992,027 A | 2/1991 | Acosta |
| 4,994,071 A | 2/1991 | MacGregor |
| 4,994,074 A | 2/1991 | Bezwada et al. |
| 4,994,077 A | 2/1991 | Dobben |
| 5,007,923 A | 4/1991 | Bezwada et al. |
| 5,017,664 A | 5/1991 | Grasel et al. |
| 5,019,085 A | 5/1991 | Hillstead |
| 5,020,612 A | 6/1991 | Williams |
| 5,024,671 A | 6/1991 | Tu et al. |
| 5,024,841 A | 6/1991 | Chu et al. |
| 5,035,706 A | 7/1991 | Gianturco et al. |
| 5,037,434 A | 8/1991 | Lane |
| 5,041,126 A | 8/1991 | Gianturco |
| 5,047,048 A | 9/1991 | Bezwada et al. |
| 5,053,008 A | 10/1991 | Bajaj |
| 5,067,491 A | 11/1991 | Taylor, II et al. |
| 5,076,807 A | 12/1991 | Bezwada et al. |
| 5,080,665 A | 1/1992 | Jarrett et al. |
| 5,080,670 A | 1/1992 | Imamura et al. |
| 5,085,629 A | 2/1992 | Goldberg et al. |
| 5,100,433 A | 3/1992 | Bezwada et al. |
| 5,103,817 A | 4/1992 | Reisdorf et al. |
| 5,104,402 A | 4/1992 | Melbin |
| 5,104,404 A | 4/1992 | Wolff |
| 5,108,420 A | 4/1992 | Marks |
| 5,108,425 A | 4/1992 | Hwang |
| 5,110,064 A | 5/1992 | Kimura et al. |
| 5,116,365 A | 5/1992 | Hillstead |
| 5,116,564 A | 5/1992 | Jansen et al. |
| 5,133,725 A | 7/1992 | Quadri |
| 5,133,755 A | 7/1992 | Brekke |
| 5,139,515 A | 8/1992 | Robicsek |
| 5,163,953 A | 11/1992 | Vince |
| 5,167,628 A | 12/1992 | Boyles |
| 5,171,259 A | 12/1992 | Inoue |
| 5,174,295 A | 12/1992 | Christian et al. |
| 5,176,692 A | 1/1993 | Wilk et al. |
| 5,178,618 A | 1/1993 | Kandarpa |
| 5,178,632 A | 1/1993 | Hanson |
| 5,178,633 A | 1/1993 | Peters |
| 5,192,301 A | 3/1993 | Kamiya et al. |
| 5,192,313 A | 3/1993 | Budd et al. |
| 5,197,979 A | 3/1993 | Quintero et al. |
| 5,197,980 A | 3/1993 | Gorshkov |
| 5,201,314 A | 4/1993 | Bosley et al. |
| 5,201,757 A | 4/1993 | Heyn et al. |
| 5,226,889 A | 7/1993 | Sheiban |
| 5,234,457 A | 8/1993 | Andersen |
| 5,239,982 A | 8/1993 | Trauthen |
| 5,258,000 A | 11/1993 | Gianturco |
| 5,275,826 A | 1/1994 | Badylak et al. |
| 5,281,422 A | 1/1994 | Badylak et al. |
| 5,282,824 A | 2/1994 | Gianturco |
| 5,284,488 A | 2/1994 | Sideris |
| 5,289,831 A | 3/1994 | Bosley |
| 5,293,879 A | 3/1994 | Vonk et al. |
| 5,306,294 A | 4/1994 | Winston et al. |
| 5,314,444 A | 5/1994 | Gianturco |
| 5,314,472 A | 5/1994 | Fontaine |
| 5,314,473 A | 5/1994 | Godin |
| 5,322,062 A | 6/1994 | Servas |
| 5,327,891 A | 7/1994 | Rammler |
| 5,334,210 A | 8/1994 | Gianturco |
| 5,334,217 A | 8/1994 | Das |
| 5,342,387 A | 8/1994 | Summers |
| 5,344,426 A | 9/1994 | Lau et al. |
| 5,352,240 A | 10/1994 | Ross |
| 5,358,518 A | 10/1994 | Camilli |
| 5,366,473 A | 11/1994 | Winston et al. |
| 5,366,479 A | 11/1994 | McGarry et al. |
| 5,370,685 A | 12/1994 | Stevens |

(56) References Cited

U.S. PATENT DOCUMENTS

| | | |
|---|---|---|
| 5,376,113 A | 12/1994 | Jansen et al. |
| 5,380,320 A | 1/1995 | Morris |
| 5,383,892 A | 1/1995 | Cardon et al. |
| 5,387,235 A | 2/1995 | Chuter |
| 5,389,106 A | 2/1995 | Tower |
| 5,393,594 A | 2/1995 | Koyfman et al. |
| 5,397,311 A | 3/1995 | Walker |
| 5,397,331 A | 3/1995 | Himpens et al. |
| 5,397,355 A | 3/1995 | Marin et al. |
| 5,405,377 A | 4/1995 | Cragg |
| 5,405,381 A | 4/1995 | Olin |
| 5,411,552 A | 5/1995 | Andersen |
| 5,412,068 A | 5/1995 | Tang et al. |
| 5,413,599 A | 5/1995 | Imachi et al. |
| 5,417,708 A | 5/1995 | Hall et al. |
| 5,421,955 A | 6/1995 | Lau et al. |
| 5,425,744 A | 6/1995 | Fagan et al. |
| 5,433,727 A | 7/1995 | Sideris |
| 5,441,515 A | 8/1995 | Khosravi et al. |
| 5,443,496 A | 8/1995 | Schwartz |
| 5,449,373 A | 9/1995 | Pinchasik |
| 5,451,235 A | 9/1995 | Lock et al. |
| 5,456,713 A | 10/1995 | Chuter |
| 5,468,253 A | 11/1995 | Bezwada et al. |
| 5,486,193 A | 1/1996 | Bourne |
| 5,486,195 A | 1/1996 | Myers et al. |
| 5,489,297 A | 2/1996 | Duran |
| 5,500,014 A | 3/1996 | Quijano |
| 5,507,767 A | 4/1996 | Maeda et al. |
| 5,507,771 A | 4/1996 | Gianturco |
| 5,514,154 A | 5/1996 | Lau et al. |
| 5,522,841 A | 6/1996 | Roby et al. |
| 5,527,354 A | 6/1996 | Fontaine et al. |
| 5,530,683 A | 6/1996 | Lindberg |
| 5,540,712 A | 7/1996 | Kleshinski et al. |
| 5,540,713 A | 7/1996 | Schnepp-Pesch et al. |
| 5,545,215 A | 8/1996 | Duran |
| 5,549,662 A | 8/1996 | Fordenbacher |
| 5,549,663 A | 8/1996 | Cottone, Jr. |
| 5,549,665 A | 8/1996 | Vesely et al. |
| 5,554,119 A | 9/1996 | Harrison et al. |
| 5,554,181 A | 9/1996 | Das |
| 5,554,185 A | 9/1996 | Block et al. |
| 5,554,389 A | 9/1996 | Badylak et al. |
| 5,562,728 A | 10/1996 | Lazarus et al. |
| 5,562,729 A | 10/1996 | Purdy |
| 5,571,168 A | 11/1996 | Toro |
| 5,589,563 A | 12/1996 | Ward et al. |
| 5,591,197 A | 1/1997 | Orth et al. |
| 5,591,198 A | 1/1997 | Boyle et al. |
| 5,595,571 A | 1/1997 | Jaffe |
| 5,603,698 A | 2/1997 | Roberts et al. |
| 5,607,442 A | 3/1997 | Fischell et al. |
| 5,607,445 A | 3/1997 | Summers |
| 5,607,465 A | 3/1997 | Camilli |
| 5,609,598 A | 3/1997 | Laufer et al. |
| 5,613,981 A | 3/1997 | Boyle et al. |
| 5,624,449 A | 4/1997 | Pham et al. |
| 5,628,791 A | 5/1997 | Bokros et al. |
| 5,630,829 A | 5/1997 | Lauterjung |
| 5,632,771 A | 5/1997 | Boatman et al. |
| 5,634,936 A | 6/1997 | Linden et al. |
| 5,636,641 A | 6/1997 | Fariabi |
| 5,641,324 A | 6/1997 | Bokros et al. |
| 5,643,312 A | 7/1997 | Fischell et al. |
| 5,643,317 A | 7/1997 | Pavcnik et al. |
| 5,653,727 A | 8/1997 | Wiktor |
| 5,662,675 A | 9/1997 | Polansky et al. |
| 5,667,523 A | 9/1997 | Bynon et al. |
| 5,668,288 A | 9/1997 | Storey et al. |
| 5,669,933 A | 9/1997 | Simon et al. |
| 5,681,346 A | 10/1997 | Orth et al. |
| 5,683,411 A | 11/1997 | Kavteladze et al. |
| 5,690,642 A | 11/1997 | Osborne et al. |
| 5,697,971 A | 12/1997 | Fischell et al. |
| 5,702,372 A | 12/1997 | Nelson |
| 5,702,421 A | 12/1997 | Schneidt |
| 5,705,181 A | 1/1998 | Cooper et al. |
| 5,707,389 A | 1/1998 | Louw et al. |
| 5,709,707 A | 1/1998 | Lock et al. |
| 5,711,969 A | 1/1998 | Patel et al. |
| 5,713,920 A | 2/1998 | Bezwada et al. |
| 5,713,950 A | 2/1998 | Cox |
| 5,713,953 A | 2/1998 | Vallana et al. |
| 5,720,777 A | 2/1998 | Jaffe |
| 5,725,519 A | 3/1998 | Penner |
| 5,725,534 A | 3/1998 | Rasmussen |
| 5,725,572 A | 3/1998 | Lam et al. |
| 5,728,158 A | 3/1998 | Lau et al. |
| 5,733,303 A | 3/1998 | Israel et al. |
| 5,733,325 A | 3/1998 | Robinson et al. |
| 5,733,337 A | 3/1998 | Carr, Jr. et al. |
| 5,735,893 A | 4/1998 | Lau et al. |
| 5,741,327 A | 4/1998 | Frantzen |
| 5,749,919 A | 5/1998 | Blanc |
| 5,755,776 A | 5/1998 | Al-Saadon |
| 5,755,777 A | 5/1998 | Chuter |
| 5,755,778 A | 5/1998 | Kleshinski |
| 5,755,781 A | 5/1998 | Jayaraman |
| 5,759,192 A | 6/1998 | Saunders |
| 5,762,625 A | 6/1998 | Igaki |
| 5,766,238 A | 6/1998 | Lau et al. |
| 5,769,780 A | 6/1998 | Hata et al. |
| 5,769,796 A | 6/1998 | Palermo et al. |
| 5,772,632 A | 6/1998 | Forman |
| 5,776,161 A | 7/1998 | Globerman |
| 5,776,188 A | 7/1998 | Shepherd et al. |
| 5,779,670 A | 7/1998 | Melman et al. |
| 5,779,729 A | 7/1998 | Severini |
| 5,792,114 A | 8/1998 | Fiore |
| 5,792,144 A | 8/1998 | Fischell et al. |
| 5,797,952 A | 8/1998 | Klein |
| 5,797,960 A | 8/1998 | Stevens et al. |
| 5,797,953 A | 9/1998 | Tekulve |
| 5,800,456 A | 9/1998 | Maeda et al. |
| 5,800,526 A | 9/1998 | Andersen et al. |
| 5,807,404 A | 9/1998 | Richter |
| 5,810,847 A | 9/1998 | Laufer et al. |
| 5,814,061 A | 9/1998 | Osborne et al. |
| 5,824,041 A | 10/1998 | Freislinger et al. |
| 5,824,042 A | 10/1998 | Lombardi et al. |
| 5,824,045 A | 10/1998 | Alt |
| 5,824,049 A | 10/1998 | Ragheb et al. |
| 5,824,062 A | 10/1998 | Patke et al. |
| 5,824,063 A | 10/1998 | Cox |
| 5,827,237 A | 10/1998 | Macoviak et al. |
| 5,833,694 A | 10/1998 | Poncet |
| 5,830,209 A | 11/1998 | Savage et al. |
| 5,833,671 A | 11/1998 | Macoviak et al. |
| 5,836,964 A | 11/1998 | Richter et al. |
| 5,840,081 A | 11/1998 | Andersen et al. |
| 5,843,090 A | 12/1998 | Schuetz |
| 5,843,117 A | 12/1998 | Alt et al. |
| 5,843,180 A | 12/1998 | Jaffe et al. |
| 5,843,181 A | 12/1998 | Jaffe et al. |
| 5,846,247 A | 12/1998 | Unworth et al. |
| 5,846,261 A | 12/1998 | Kotula et al. |
| 5,851,232 A | 12/1998 | Lois |
| 5,853,422 A | 12/1998 | Huebsch et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,861,003 A | 1/1999 | Latson et al. |
| 5,865,723 A | 2/1999 | Love |
| 5,876,445 A | 3/1999 | Andersen et al. |
| 5,876,448 A | 3/1999 | Thompson et al. |
| 5,879,305 A | 3/1999 | Yock et al. |
| 5,879,366 A | 3/1999 | Shaw et al. |
| 5,879,382 A | 3/1999 | Boneau |
| 5,885,619 A | 3/1999 | Patel et al. |
| 5,891,128 A | 4/1999 | Gia et al. |
| 5,891,193 A | 4/1999 | Robinson et al. |
| 5,891,195 A | 4/1999 | Klostermeyer et al. |

(56) References Cited

U.S. PATENT DOCUMENTS

| | | |
|---|---|---|
| 5,895,419 A | 4/1999 | Tweden et al. |
| 5,895,420 A | 4/1999 | Mirsch, II et al. |
| 5,902,334 A | 5/1999 | Dwyer et al. |
| 5,907,893 A | 6/1999 | Zadno-Azizi et al. |
| 5,908,452 A | 6/1999 | Bokros et al. |
| 5,911,732 A | 6/1999 | Hojeibane |
| 5,925,063 A | 7/1999 | Khosravi |
| 5,926,016 A | 7/1999 | Pattantyus |
| 5,928,248 A | 7/1999 | Acker |
| 5,928,258 A | 7/1999 | Kahn |
| 5,935,148 A | 8/1999 | Villar et al. |
| 5,935,161 A | 8/1999 | Robinson |
| 5,937,861 A | 8/1999 | Augustine |
| 5,938,682 A | 8/1999 | Hojeibane |
| 5,944,733 A | 8/1999 | Engelson |
| 5,944,738 A | 8/1999 | Amplatz et al. |
| 5,947,995 A | 9/1999 | Samuels |
| 5,947,997 A | 9/1999 | Pavcnik et al. |
| 5,954,766 A | 9/1999 | Zadno-Azizi et al. |
| 5,955,110 A | 9/1999 | Patel et al. |
| 5,957,949 A | 9/1999 | Leonhardt et al. |
| 5,960,642 A | 10/1999 | Kim et al. |
| 5,961,546 A | 10/1999 | Robinson et al. |
| 5,968,096 A | 10/1999 | Whitson et al. |
| 5,980,565 A | 11/1999 | Jayaraman |
| 5,980,799 A | 11/1999 | Martakos et al. |
| 5,981,195 A | 11/1999 | Fuller et al. |
| 5,993,844 A | 11/1999 | Abraham et al. |
| 5,997,573 A | 12/1999 | Quijano et al. |
| 6,004,347 A | 12/1999 | McNamara et al. |
| 6,007,521 A | 12/1999 | Melman |
| 6,010,531 A | 1/2000 | Donlon et al. |
| 6,015,431 A | 1/2000 | Thornton et al. |
| 6,017,363 A | 1/2000 | Hojeibane |
| 6,022,359 A | 2/2000 | Frantzen et al. |
| 6,022,374 A | 2/2000 | Imran |
| 6,024,690 A | 2/2000 | Lee et al. |
| 6,027,525 A | 2/2000 | Suh et al. |
| 6,033,398 A | 3/2000 | Farley et al. |
| 6,036,687 A | 3/2000 | Laufer et al. |
| 6,042,606 A | 3/2000 | Frantzen |
| 6,053,940 A | 4/2000 | Wijay |
| 6,056,775 A | 5/2000 | Borghi et al. |
| 6,059,757 A | 5/2000 | Macoviak et al. |
| 6,059,779 A | 5/2000 | Mills |
| 6,059,826 A | 5/2000 | Bokros |
| 6,059,827 A | 5/2000 | Fenton |
| 6,063,113 A | 5/2000 | Kavteladze et al. |
| 6,074,419 A | 6/2000 | Healy et al. |
| 6,077,280 A | 6/2000 | Das |
| 6,077,291 A | 6/2000 | Das |
| 6,077,295 A | 6/2000 | Limon et al. |
| 6,077,296 A | 6/2000 | Shokoohi et al. |
| 6,080,182 A | 6/2000 | Shaw et al. |
| 6,090,035 A | 7/2000 | Campbell |
| 6,090,127 A | 7/2000 | Globerman |
| 6,096,027 A | 8/2000 | Layne |
| 6,096,052 A | 8/2000 | Callister et al. |
| 6,096,070 A | 8/2000 | Ragheb et al. |
| 6,099,561 A | 8/2000 | Alt |
| 6,099,567 A | 8/2000 | Badylak et al. |
| 6,100,962 A | 8/2000 | Kinoshita et al. |
| 6,110,191 A | 8/2000 | Dehdashtian |
| 6,110,201 A | 8/2000 | Quijano et al. |
| 6,110,212 A | 8/2000 | Gregory |
| 6,113,623 A | 9/2000 | Sgro |
| 6,117,157 A | 9/2000 | Tekulve |
| 6,117,159 A | 9/2000 | Huebsch et al. |
| 6,117,979 A | 9/2000 | Hendriks et al. |
| 6,123,721 A | 9/2000 | Jang |
| 6,126,685 A | 10/2000 | Lenker |
| 6,126,686 A | 10/2000 | Badylak et al. |
| 6,129,755 A | 10/2000 | Mathis et al. |
| 6,132,460 A | 10/2000 | Thompson |
| 6,132,461 A | 10/2000 | Thompson |
| 6,136,025 A | 10/2000 | Barbut et al. |
| 6,139,575 A | 10/2000 | Shu et al. |
| 6,143,016 A | 11/2000 | Bleam |
| 6,143,022 A | 11/2000 | Shull et al. |
| 6,146,416 A | 11/2000 | Andersen et al. |
| 6,149,660 A | 11/2000 | Laufer et al. |
| 6,149,680 A | 11/2000 | Shelso |
| 6,159,237 A | 12/2000 | Alt et al. |
| 6,162,245 A | 12/2000 | Jayaraman |
| 6,168,614 B1 | 1/2001 | Andersen et al. |
| 6,168,617 B1 | 1/2001 | Blaeser et al. |
| 6,174,331 B1 | 1/2001 | Moe et al. |
| 6,176,875 B1 | 1/2001 | Lenker |
| 6,178,968 B1 | 1/2001 | Louw et al. |
| 6,179,858 B1 | 1/2001 | Squire et al. |
| 6,183,511 B1 | 2/2001 | Patke et al. |
| 6,183,512 B1 | 2/2001 | Howanec et al. |
| 6,187,036 B1 | 2/2001 | Shaolian et al. |
| 6,187,039 B1 | 2/2001 | Hiles et al. |
| 6,190,406 B1 | 2/2001 | Duerig et al. |
| 6,193,731 B1 | 2/2001 | Oppelt |
| 6,197,049 B1 | 3/2001 | Shaolian et al. |
| 6,200,336 B1 | 3/2001 | Pavcnik et al. |
| 6,206,907 B1 | 3/2001 | Marino et al. |
| 6,206,931 B1 | 3/2001 | Cook et al. |
| 6,214,029 B1 | 4/2001 | Thill et al. |
| 6,216,493 B1 | 4/2001 | Weston et al. |
| 6,221,091 B1 | 4/2001 | Khosravi |
| 6,231,507 B1 | 5/2001 | Zikorus et al. |
| 6,231,561 B1 | 5/2001 | Frazier et al. |
| 6,231,598 B1 | 5/2001 | Berry |
| 6,235,050 B1 | 5/2001 | Quiachon et al. |
| 6,235,053 B1 | 5/2001 | Jang |
| 6,238,409 B1 | 5/2001 | Hojeibane |
| 6,238,416 B1 | 5/2001 | Sideris |
| 6,241,763 B1 | 6/2001 | Drasler et al. |
| 6,245,102 B1 | 6/2001 | Jayaraman |
| 6,254,611 B1 | 7/2001 | Vrba |
| 6,254,631 B1 | 7/2001 | Thompson |
| 6,254,636 B1 | 7/2001 | Peredo |
| 6,254,642 B1 | 7/2001 | Taylor |
| 6,264,700 B1 | 7/2001 | Kilcoyne et al. |
| 6,280,467 B1 | 8/2001 | Leonhardt |
| 6,233,968 B1 | 9/2001 | Taheri |
| 6,283,990 B1 | 9/2001 | Kanesaka |
| 6,287,330 B1 | 9/2001 | Johansson et al. |
| 6,287,332 B1 | 9/2001 | Bolz et al. |
| 6,287,334 B1 | 9/2001 | Moll et al. |
| 6,287,336 B1 | 9/2001 | Globerman et al. |
| 6,293,966 B1 | 9/2001 | Frantzen |
| 6,296,657 B1 | 10/2001 | Brucker |
| 6,299,604 B1 | 10/2001 | Ragheb et al. |
| 6,299,635 B1 | 10/2001 | Frantzen |
| 6,299,636 B1 | 10/2001 | Schmitt et al. |
| 6,299,637 B1 * | 10/2001 | Shaolian ............... A61F 2/2418 623/1.24 |
| 6,312,465 B1 | 11/2001 | Griffin et al. |
| 6,312,474 B1 | 11/2001 | Francis et al. |
| 6,312,549 B1 | 11/2001 | Huang et al. |
| 6,315,793 B1 | 11/2001 | Bokros et al. |
| 6,319,281 B1 | 11/2001 | Patel |
| 6,325,819 B1 | 12/2001 | Pavcnik et al. |
| 6,328,727 B1 | 12/2001 | Frazier et al. |
| 6,328,763 B1 | 12/2001 | Love et al. |
| 6,334,052 B1 | 12/2001 | Nordstrand |
| 6,334,871 B1 | 1/2002 | Dor et al. |
| 6,334,872 B1 | 1/2002 | Termin et al. |
| 6,336,938 B1 | 1/2002 | Kavteladze et al. |
| 6,338,730 B1 | 1/2002 | Bonutti et al. |
| 6,338,740 B1 | 1/2002 | Carpentier |
| 6,340,366 B2 | 1/2002 | Wijay |
| 6,342,067 B1 | 1/2002 | Mathis et al. |
| 6,342,070 B1 | 1/2002 | Nguyen-Thien-Nhon |
| 6,346,074 B1 | 2/2002 | Roth |
| 6,348,065 B1 | 2/2002 | Brown et al. |
| 6,352,554 B2 | 3/2002 | De Paulis |
| 6,355,052 B1 | 3/2002 | Neuss et al. |
| 6,355,056 B1 | 3/2002 | Pinheiro |
| 6,355,070 B1 | 3/2002 | Andersen et al. |

(56) References Cited

U.S. PATENT DOCUMENTS

| | | |
|---|---|---|
| 6,358,228 B1 | 3/2002 | Tubman et al. |
| 6,358,277 B1 | 3/2002 | Duran |
| 6,358,284 B1 | 3/2002 | Fearnot et al. |
| 6,368,338 B1 | 4/2002 | Konya et al. |
| 6,371,961 B1 | 4/2002 | Osborne et al. |
| 6,371,983 B1 | 4/2002 | Lane |
| 6,375,679 B1 | 4/2002 | Martyn et al. |
| 6,375,989 B1 | 4/2002 | Badylak et al. |
| 6,379,365 B1 | 4/2002 | Diaz |
| 6,379,710 B1 | 4/2002 | Badylak |
| 6,383,216 B1 | 5/2002 | Kavteladze et al. |
| 6,383,832 B1 | 5/2002 | Stone |
| 6,395,018 B1 | 5/2002 | Castaneda |
| 6,409,752 B1 | 6/2002 | Boatman et al. |
| 6,415,631 B1 | 7/2002 | Weston et al. |
| 6,416,542 B1 | 7/2002 | Marcade et al. |
| 6,425,914 B1 | 7/2002 | Wallace et al. |
| 6,425,916 B1 | 7/2002 | Garrison |
| 6,428,570 B1 | 8/2002 | Globerman |
| 6,440,163 B1 | 8/2002 | Swanson et al. |
| 6,440,164 B1 | 8/2002 | DiMatteo et al. |
| 6,444,229 B2 | 9/2002 | Voytik-Harbin et al. |
| 6,451,052 B1 | 9/2002 | Burmeister et al. |
| 6,458,137 B1 | 10/2002 | Klint |
| 6,458,153 B1 | 10/2002 | Bailey et al. |
| 6,461,382 B1 | 10/2002 | Cao |
| 6,464,720 B2 | 10/2002 | Boatman |
| 6,471,718 B1 | 10/2002 | Staehle |
| 6,478,819 B2 | 11/2002 | Moe |
| 6,482,228 B1 | 11/2002 | Norred |
| 6,485,500 B1 | 11/2002 | Kokish et al. |
| 6,485,510 B1 | 11/2002 | Camrud et al. |
| 6,488,702 B1 | 12/2002 | Besselink |
| 6,494,909 B2 | 12/2002 | Greenhalgh |
| 6,503,272 B2 | 1/2003 | Duerig et al. |
| 6,508,824 B1 | 1/2003 | Flaherty et al. |
| 6,508,833 B2 | 1/2003 | Pavcnik |
| 6,508,966 B1 | 1/2003 | Castro et al. |
| 6,514,063 B2 | 2/2003 | Acciai et al. |
| 6,524,336 B1 | 2/2003 | Papazoglou et al. |
| 6,527,800 B1 | 3/2003 | McGuckin, Jr. et al. |
| 6,530,951 B1 | 3/2003 | Bates et al. |
| 6,533,807 B2 | 3/2003 | Wolinsky et al. |
| 6,544,291 B2 | 4/2003 | Taylor |
| 6,547,815 B2 | 4/2003 | Myers et al. |
| 6,553,801 B2 | 4/2003 | Chen |
| 6,558,415 B2 | 5/2003 | Thompson |
| 6,558,418 B2 | 5/2003 | Carpentier et al. |
| 6,558,429 B2 | 5/2003 | Taylor |
| 6,562,065 B1 | 5/2003 | Shanley |
| 6,565,597 B1 | 5/2003 | Fearnot et al. |
| 6,565,600 B2 | 5/2003 | Hojeibane |
| 6,572,650 B1 | 6/2003 | Abraham et al. |
| 6,579,221 B1 | 6/2003 | Peterson |
| 6,579,307 B2 | 6/2003 | Sarac |
| 6,579,311 B1 | 6/2003 | Makower |
| 6,579,538 B1 | 6/2003 | Spievack |
| 6,580,568 B2 | 6/2003 | Ozaki |
| 6,582,462 B1 | 6/2003 | Andersen et al. |
| 6,585,761 B2 | 7/2003 | Taheri |
| 6,589,230 B2 | 7/2003 | Gla et al. |
| 6,594,880 B2 | 7/2003 | Elsberry |
| 6,596,021 B1 | 7/2003 | Lootz |
| 6,598,307 B2 | 7/2003 | Love et al. |
| 6,599,275 B1 | 7/2003 | Fischer, Jr. |
| 6,602,241 B2 | 8/2003 | Makower et al. |
| 6,602,286 B1 | 8/2003 | Strecker |
| 6,605,049 B1 | 8/2003 | Wagner et al. |
| 6,613,002 B1 | 9/2003 | Clark et al. |
| 6,613,086 B1 | 9/2003 | Moe et al. |
| 6,616,680 B1 | 9/2003 | Thielen |
| 6,623,506 B2 | 9/2003 | McGuckin, Jr. et al. |
| 6,623,508 B2 | 9/2003 | Shaw et al. |
| 6,632,196 B1 | 10/2003 | Houser |
| 6,638,300 B1 | 10/2003 | Frantzen |
| 6,640,412 B2 | 11/2003 | Iancea |
| 6,656,206 B2 | 12/2003 | Corcoran et al. |
| 6,656,216 B1 | 12/2003 | Hossainy et al. |
| 6,663,661 B2 | 12/2003 | Boneau |
| 6,666,885 B2 | 12/2003 | Moe |
| 6,666,886 B1 | 12/2003 | Tranquillo et al. |
| 6,669,724 B2 | 12/2003 | Park et al. |
| 6,673,100 B2 | 1/2004 | Diaz et al. |
| 6,676,694 B1 | 1/2004 | Weiss |
| 6,676,698 B2 | 1/2004 | McGuckin, Jr. et al. |
| 6,678,962 B1 | 1/2004 | Love et al. |
| 6,685,739 B2 | 2/2004 | DiMatteo et al. |
| 6,689,123 B2 | 2/2004 | Pinchasik |
| 6,692,458 B2 | 2/2004 | Forman et al. |
| 6,706,026 B1 | 3/2004 | Goldstein et al. |
| 6,716,241 B2 | 4/2004 | Wilder et al. |
| 6,720,402 B2 | 4/2004 | Langer et al. |
| 6,726,715 B2 | 4/2004 | Sutherland |
| 6,730,064 B2 | 5/2004 | Ragheb et al. |
| 6,730,117 B1 | 5/2004 | Tseng et al. |
| 6,730,118 B2 | 5/2004 | Spenser et al. |
| 6,733,525 B2 | 5/2004 | Yang et al. |
| 6,746,489 B2 | 6/2004 | Dua et al. |
| 6,749,622 B2 | 6/2004 | McGuckin, Jr. et al. |
| 6,752,826 B2 | 6/2004 | Holloway et al. |
| 6,752,828 B2 | 6/2004 | Thornton |
| 6,761,735 B2 | 7/2004 | Eberhardt et al. |
| 6,767,362 B2 | 7/2004 | Schreck |
| 6,783,499 B2 | 8/2004 | Schwartz |
| 6,786,922 B2 | 9/2004 | Schaeffer |
| 6,790,214 B2 | 9/2004 | Kraemer et al. |
| 6,790,218 B2 | 9/2004 | Jayaraman |
| 6,790,237 B2 | 9/2004 | Stinson |
| 6,821,292 B2 | 11/2004 | Pazienza et al. |
| 6,823,576 B2 | 11/2004 | Austin |
| 6,830,584 B1 | 12/2004 | Seguin |
| 6,843,802 B1 | 1/2005 | Villalobos et al. |
| 6,859,986 B2 | 3/2005 | Jackson |
| 6,878,162 B2 | 4/2005 | Bales et al. |
| 6,896,690 B1 | 5/2005 | Lambrecht |
| 6,908,481 B2 | 6/2005 | Cribier |
| 6,911,037 B2 | 6/2005 | Gainor et al. |
| 6,915,560 B2 | 7/2005 | Austin |
| 6,918,929 B2 | 7/2005 | Udipi et al. |
| 6,921,378 B2 | 7/2005 | O'Keefe et al. |
| 6,932,829 B2 | 8/2005 | Majercak |
| 6,939,377 B2 | 9/2005 | Jayaraman et al. |
| 6,945,978 B1 | 9/2005 | Hyde |
| 6,945,989 B1 | 9/2005 | Betelia et al. |
| 6,949,113 B2 | 9/2005 | Van Tassel et al. |
| 6,949,116 B2 | 9/2005 | Solymar et al. |
| 6,953,332 B1 | 10/2005 | Kurk et al. |
| 6,958,076 B2 | 10/2005 | Acosta |
| 6,960,220 B2 | 11/2005 | Marino et al. |
| 6,962,603 B1 | 11/2005 | Brown et al. |
| 6,974,474 B2 | 12/2005 | Pavcnik et al. |
| 6,976,995 B2 | 12/2005 | Mathis et al. |
| 6,994,092 B2 | 2/2006 | Van der Burg et al. |
| 6,994,717 B2 | 2/2006 | Konya et al. |
| 7,011,671 B2 | 3/2006 | Welch |
| 7,018,403 B1 | 3/2006 | Pienknagura |
| 7,018,404 B2 | 3/2006 | Holmberg et al. |
| 7,018,406 B2 | 3/2006 | Seguin |
| 7,018,407 B1 | 3/2006 | Wright et al. |
| 7,025,777 B2 | 4/2006 | Moore |
| 7,025,780 B2 | 4/2006 | Gabbay |
| 7,025,923 B2 | 4/2006 | Harhen et al. |
| 7,029,493 B2 | 4/2006 | Majercak et al. |
| 7,044,966 B2 | 5/2006 | Svanidze et al. |
| 7,060,088 B1 | 6/2006 | Fischell et al. |
| 7,070,616 B2 | 7/2006 | Majercak et al. |
| 7,081,131 B2 | 7/2006 | Thornton |
| 7,101,381 B2 | 9/2006 | Ford et al. |
| 7,101,395 B2 | 9/2006 | Tremulis et al. |
| 7,101,396 B2 | 9/2006 | Svanidze et al. |
| 7,118,600 B2 | 10/2006 | Dua et al. |
| 7,125,418 B2 | 10/2006 | Duran et al. |
| 7,128,073 B1 | 10/2006 | van der Burg et al. |
| 7,128,756 B2 | 10/2006 | Lowe et al. |

(56) References Cited

U.S. PATENT DOCUMENTS

| | | |
|---|---|---|
| 7,128,757 B2 | 10/2006 | Osborne et al. |
| 7,128,759 B2 | 10/2006 | Osborne et al. |
| 7,144,410 B2 | 12/2006 | Marino et al. |
| 7,147,661 B2 | 12/2006 | Chobotov et al. |
| 7,153,324 B2 | 12/2006 | Case et al. |
| 7,160,320 B2 | 1/2007 | Duran |
| 7,163,556 B2 | 1/2007 | Xie et al. |
| 7,172,625 B2 | 2/2007 | Shu et al. |
| 7,179,270 B2 | 2/2007 | Makower |
| 7,182,779 B2 | 2/2007 | Acosta et al. |
| 7,186,789 B2 | 3/2007 | Hossainy et al. |
| 7,195,641 B2 | 3/2007 | Palmaz et al. |
| 7,232,462 B2 | 6/2007 | Schaeffer |
| 7,247,167 B2 | 7/2007 | Gabbay |
| 7,258,697 B1 | 8/2007 | Cox et al. |
| 7,261,732 B2 | 8/2007 | Justino |
| 7,273,492 B2 | 9/2007 | Cheng et al. |
| 7,288,105 B2 | 10/2007 | Oman et al. |
| 7,303,571 B2 | 12/2007 | Makower et al. |
| 7,323,010 B2 | 1/2008 | Verona et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,354,455 B2 | 4/2008 | Stinson |
| 7,361,189 B2 | 4/2008 | Case et al. |
| 7,364,587 B2 | 4/2008 | Dong et al. |
| 7,377,938 B2 | 5/2008 | Sarac et al. |
| 7,381,219 B2 | 6/2008 | Salahieh et al. |
| 7,399,315 B2 | 7/2008 | Iobbi |
| 7,402,171 B2 | 7/2008 | Osborne |
| 7,435,257 B2 | 10/2008 | Lashinski et al. |
| 7,445,630 B2 | 11/2008 | Lashinski et al. |
| 7,445,631 B2 | 11/2008 | Salahieh et al. |
| 7,452,371 B2 | 11/2008 | Pavcnik et al. |
| 7,491,942 B2 | 2/2009 | Black et al. |
| 7,503,928 B2 | 3/2009 | Case et al. |
| 7,520,894 B2 | 4/2009 | Pavcnik et al. |
| 7,524,331 B2 | 4/2009 | Birdsall |
| 7,524,332 B2 | 4/2009 | Osborne et al. |
| 7,534,259 B2 | 5/2009 | Lashinski et al. |
| 7,544,205 B2 | 6/2009 | Flagle et al. |
| 7,544,207 B2 | 6/2009 | Osborne et al. |
| 7,547,322 B2 | 6/2009 | Sarac et al. |
| 7,556,645 B2 | 7/2009 | Lashinski et al. |
| 7,563,276 B2 | 7/2009 | Osborne et al. |
| 7,563,277 B2 | 7/2009 | Case et al. |
| 7,566,336 B2 | 7/2009 | Corcoran et al. |
| 7,569,071 B2 | 8/2009 | Haverkost et al. |
| 7,582,110 B2 | 9/2009 | Case et al. |
| 7,585,321 B2 | 9/2009 | Cribier |
| 7,594,927 B2 | 9/2009 | Majercak et al. |
| 7,604,661 B2 | 10/2009 | Pavcnik et al. |
| 7,618,447 B2 | 11/2009 | Case et al. |
| 7,625,395 B2 | 12/2009 | Case et al. |
| 7,625,399 B2 | 12/2009 | Case et al. |
| 7,628,803 B2 | 12/2009 | Pavcnik et al. |
| 7,628,804 B2 | 12/2009 | Flagle et al. |
| 7,637,937 B2 | 12/2009 | Case et al. |
| 7,641,686 B2 | 1/2010 | Lashinski et al. |
| 7,648,527 B2 | 1/2010 | Agnew |
| 7,653,455 B2 | 1/2010 | Cinader, Jr. |
| 7,655,288 B2 | 2/2010 | Bauman et al. |
| 7,655,584 B2 | 2/2010 | Biran et al. |
| 7,658,759 B2 | 2/2010 | Case et al. |
| 7,658,762 B2 | 2/2010 | Lashinski et al. |
| 7,659,219 B2 | 2/2010 | Biran et al. |
| 7,670,366 B2 | 3/2010 | Case et al. |
| 7,678,144 B2 | 3/2010 | Bailey et al. |
| 7,686,844 B2 | 3/2010 | Case et al. |
| 7,736,385 B2 | 6/2010 | Agnew |
| 7,739,971 B2 | 6/2010 | Chambers et al. |
| 7,745,532 B2 | 6/2010 | Ruberti et al. |
| 7,806,921 B2 | 10/2010 | Hoffman |
| 7,815,923 B2 | 10/2010 | Johnson et al. |
| 7,819,836 B2 | 10/2010 | Levine et al. |
| 7,846,199 B2 | 12/2010 | Paul, Jr. et al. |
| 7,846,203 B2 | 12/2010 | Cribier |
| 7,850,510 B2 | 12/2010 | Farnsworth et al. |
| 7,854,759 B2 | 12/2010 | Shirley |
| 7,861,570 B2 | 1/2011 | Thomas |
| 7,871,430 B2 | 1/2011 | Pavcnik et al. |
| 7,918,882 B2 | 4/2011 | Pavcnik et al. |
| 7,935,144 B2 | 5/2011 | Lashinski et al. |
| 7,942,887 B2 | 5/2011 | Kraemer et al. |
| 7,955,375 B2 | 6/2011 | Agnew |
| 7,955,376 B2 | 6/2011 | Osborne et al. |
| 7,955,377 B2 | 6/2011 | Melsheimer |
| 7,964,206 B2 | 6/2011 | Suokas et al. |
| 7,979,150 B2 | 7/2011 | Lin et al. |
| 7,993,410 B2 | 8/2011 | Shin et al. |
| 8,012,201 B2 | 9/2011 | Lashinski et al. |
| 8,038,708 B2 | 10/2011 | Case et al. |
| 8,038,710 B2 | 10/2011 | Fearnot et al. |
| 8,048,500 B2 | 11/2011 | Drumheller et al. |
| 8,048,503 B2 | 11/2011 | Farnsworth et al. |
| 8,057,532 B2 | 11/2011 | Hoffman |
| 8,057,540 B2 | 11/2011 | Letac et al. |
| 8,092,522 B2 | 1/2012 | Paul, Jr. et al. |
| 8,109,990 B2 | 2/2012 | Paul et al. |
| 8,118,877 B2 | 2/2012 | Brauker et al. |
| 8,128,686 B2 | 3/2012 | Paul, Jr. et al. |
| 8,129,477 B1 | 3/2012 | Zhang et al. |
| 8,133,213 B2 | 3/2012 | Lashinski et al. |
| 8,133,500 B2 | 3/2012 | Ringeisen et al. |
| 8,157,810 B2 | 4/2012 | Case et al. |
| 8,157,857 B2 | 4/2012 | Case et al. |
| 8,197,534 B2 | 6/2012 | Osborne et al. |
| 8,211,165 B1 | 7/2012 | McIntosh et al. |
| 8,221,492 B2 | 7/2012 | Case et al. |
| 8,252,043 B2 | 8/2012 | Case et al. |
| 8,257,429 B2 | 9/2012 | Pavcnik |
| 8,273,117 B2 | 9/2012 | Palumbo et al. |
| 8,276,533 B2 | 10/2012 | Chambers et al. |
| 8,292,938 B2 | 10/2012 | Case |
| 8,303,648 B2 | 11/2012 | Grewe et al. |
| 8,303,649 B2 | 11/2012 | Agnew et al. |
| 8,308,796 B2 | 11/2012 | Lashinski et al. |
| 8,313,526 B2 | 11/2012 | Hoffman et al. |
| 8,317,853 B2 | 11/2012 | Agnew |
| 8,323,332 B2 | 12/2012 | Agnew |
| 8,337,545 B2 | 12/2012 | Osborne |
| 8,351,126 B2 | 1/2013 | Peng |
| 8,366,741 B2 | 2/2013 | Chin et al. |
| 8,366,743 B2 | 2/2013 | Zeng |
| 8,377,118 B2 | 2/2013 | Lashinski et al. |
| 8,403,977 B2 | 3/2013 | Case et al. |
| 8,403,979 B2 | 3/2013 | Paul, Jr. |
| 8,470,020 B2 | 6/2013 | Schaeffer et al. |
| 8,475,512 B2 | 7/2013 | Hunt |
| 8,475,516 B2 | 7/2013 | Paul et al. |
| 8,506,621 B2 | 8/2013 | Agnew et al. |
| 8,556,881 B2 | 10/2013 | Lashinski et al. |
| 8,568,477 B2 | 10/2013 | Lashinski et al. |
| 8,617,205 B2 | 12/2013 | Pavcnik et al. |
| 8,652,197 B2 | 2/2014 | Paul et al. |
| 8,663,320 B2 | 3/2014 | Chambers et al. |
| 8,679,175 B2 | 3/2014 | Paul, Jr. et al. |
| 8,702,746 B2 | 4/2014 | Tekulve et al. |
| 8,771,338 B2 | 7/2014 | Schaeffer et al. |
| 10,722,365 B2 * | 7/2020 | Chambers ............. A61F 2/2475 |
| 2001/0001128 A1 | 5/2001 | Holman et al. |
| 2001/0004707 A1 | 6/2001 | Dereume et al. |
| 2001/0004715 A1 * | 6/2001 | Duran ................. A61L 27/3604 623/23.72 |
| 2001/0007956 A1 | 7/2001 | Letac et al. |
| 2001/0011187 A1 | 8/2001 | Pavcnik et al. |
| 2001/0016770 A1 | 8/2001 | Allen et al. |
| 2001/0018610 A1 | 8/2001 | Limon |
| 2001/0020189 A1 | 9/2001 | Taylor |
| 2001/0020190 A1 | 9/2001 | Taylor |
| 2001/0021872 A1 | 9/2001 | Bailey et al. |
| 2001/0025197 A1 | 9/2001 | Shu et al. |
| 2001/0034537 A1 | 10/2001 | Shaw et al. |
| 2001/0037129 A1 | 11/2001 | Thill |

(56) References Cited

U.S. PATENT DOCUMENTS

| | | | |
|---|---|---|---|
| 2001/0039450 A1* | 11/2001 | Pavcnik | A61F 2/2475 623/1.24 |
| 2001/0041930 A1 | 11/2001 | Globerman et al. | |
| 2001/0044648 A1 | 11/2001 | Wolinsky et al. | |
| 2001/0049553 A1 | 12/2001 | De Paulis et al. | |
| 2002/0002400 A1 | 1/2002 | Drasler et al. | |
| 2002/0019665 A1 | 2/2002 | Dehdashtian et al. | |
| 2002/0029994 A1 | 3/2002 | Schon | |
| 2002/0032414 A1 | 3/2002 | Ragheb et al. | |
| 2002/0032481 A1* | 3/2002 | Gabbay | A61F 2/2475 623/2.11 |
| 2002/0038128 A1 | 3/2002 | Turovkiy et al. | |
| 2002/0052642 A1 | 5/2002 | Cox et al. | |
| 2002/0052651 A1 | 5/2002 | Myers et al. | |
| 2002/0055772 A1 | 5/2002 | McGuckin, Jr. et al. | |
| 2002/0065552 A1 | 5/2002 | Jayaraman et al. | |
| 2002/0065554 A1 | 5/2002 | Streeter | |
| 2002/0068866 A1 | 6/2002 | Zikorus | |
| 2002/0072794 A1 | 6/2002 | Gabbay | |
| 2002/0099439 A1 | 7/2002 | Schwartz et al. | |
| 2002/0111339 A1 | 8/2002 | Klausener et al. | |
| 2002/0111647 A1 | 8/2002 | Khairkhahan et al. | |
| 2002/0115559 A1 | 8/2002 | Batchelor et al. | |
| 2002/0120338 A1 | 8/2002 | Boyer et al. | |
| 2002/0123786 A1 | 9/2002 | Gittings | |
| 2002/0123790 A1 | 9/2002 | White et al. | |
| 2002/0123800 A1 | 9/2002 | Taheri | |
| 2002/0123802 A1 | 9/2002 | Snyders | |
| 2002/0129820 A1 | 9/2002 | Ryan et al. | |
| 2002/0138131 A1 | 9/2002 | Solovay et al. | |
| 2002/0138135 A1 | 9/2002 | Duerig et al. | |
| 2002/0169475 A1 | 11/2002 | Gainor et al. | |
| 2002/0173843 A1 | 11/2002 | Peredo et al. | |
| 2002/0177890 A1 | 11/2002 | Lenker | |
| 2002/0177894 A1 | 11/2002 | Acosta et al. | |
| 2002/0177899 A1 | 11/2002 | Eum | |
| 2002/0179098 A1 | 12/2002 | Makower | |
| 2002/0183787 A1 | 12/2002 | Wahr et al. | |
| 2002/0187288 A1 | 12/2002 | Lim et al. | |
| 2002/0193871 A1 | 12/2002 | Beyersdorf et al. | |
| 2002/0198563 A1 | 12/2002 | Gainor et al. | |
| 2003/0014104 A1 | 1/2003 | Cribier | |
| 2003/0014126 A1 | 1/2003 | Patel et al. | |
| 2003/0018968 A1 | 1/2003 | Avnet | |
| 2003/0023302 A1 | 1/2003 | Moe et al. | |
| 2003/0023303 A1 | 1/2003 | Palmaz et al. | |
| 2003/0028213 A1 | 2/2003 | Thill et al. | |
| 2003/0028233 A1 | 2/2003 | Vardi et al. | |
| 2003/0033009 A1 | 2/2003 | Gabbay | |
| 2003/0036794 A1 | 2/2003 | Ragheb et al. | |
| 2003/0040792 A1* | 2/2003 | Gabbay | A61F 2/2436 623/2.11 |
| 2003/0040808 A1 | 2/2003 | Stack et al. | |
| 2003/0055483 A1 | 3/2003 | Gumm | |
| 2003/0055492 A1* | 3/2003 | Shaolian | A61F 2/2475 623/1.24 |
| 2003/0055496 A1 | 3/2003 | Cai et al. | |
| 2003/0069646 A1 | 4/2003 | Stinson | |
| 2003/0083730 A1 | 5/2003 | Stinson | |
| 2003/0083741 A1 | 5/2003 | Woo et al. | |
| 2003/0093071 A1 | 5/2003 | Hauck et al. | |
| 2003/0093108 A1 | 5/2003 | Avellanet et al. | |
| 2003/0093144 A1 | 5/2003 | Jang | |
| 2003/0097172 A1 | 5/2003 | Shalev et al. | |
| 2003/0109922 A1 | 6/2003 | Peterson et al. | |
| 2003/0114913 A1* | 6/2003 | Spenser | A61F 2/2412 623/1.11 |
| 2003/0114919 A1 | 6/2003 | McQuiston et al. | |
| 2003/0120263 A1 | 6/2003 | Ouriel et al. | |
| 2003/0125790 A1 | 7/2003 | Fastovsky et al. | |
| 2003/0125791 A1 | 7/2003 | Sequin et al. | |
| 2003/0125795 A1 | 7/2003 | Pavcnik et al. | |
| 2003/0130713 A1 | 7/2003 | Stewart et al. | |
| 2003/0130726 A1 | 7/2003 | Thorpe et al. | |
| 2003/0135266 A1 | 7/2003 | Chew et al. | |
| 2003/0139805 A1 | 7/2003 | Holmberg et al. | |
| 2003/0139819 A1 | 7/2003 | Beer et al. | |
| 2003/0144670 A1 | 7/2003 | Pavcnik et al. | |
| 2003/0144694 A1 | 7/2003 | Chanduszko et al. | |
| 2003/0149471 A1 | 8/2003 | Briana et al. | |
| 2003/0153972 A1 | 8/2003 | Helmus | |
| 2003/0153974 A1 | 8/2003 | Spenser et al. | |
| 2003/0163190 A1 | 8/2003 | LaFont et al. | |
| 2003/0171824 A1 | 9/2003 | Abraham et al. | |
| 2003/0176911 A1 | 9/2003 | Iancea et al. | |
| 2003/0176912 A1 | 9/2003 | Chuter et al. | |
| 2003/0176914 A1 | 9/2003 | Rabkin et al. | |
| 2003/0181968 A1 | 9/2003 | Xie et al. | |
| 2003/0181973 A1 | 9/2003 | Sahota | |
| 2003/0181974 A1 | 9/2003 | Xie et al. | |
| 2003/0187500 A1 | 10/2003 | Jansen et al. | |
| 2003/0191495 A1 | 10/2003 | Ryan et al. | |
| 2003/0191525 A1 | 10/2003 | Thornton | |
| 2003/0195618 A1 | 10/2003 | Abraham et al. | |
| 2003/0199747 A1 | 10/2003 | Michlitsch | |
| 2003/0199767 A1 | 10/2003 | Cespedes | |
| 2003/0199768 A1 | 10/2003 | Cespedes | |
| 2003/0206860 A1 | 11/2003 | Bleyer et al. | |
| 2003/0208224 A1 | 11/2003 | Broome | |
| 2003/0208254 A1 | 11/2003 | Shortt | |
| 2003/0208261 A1* | 11/2003 | Thorpe | A61F 2/2475 623/1.16 |
| 2003/0209835 A1* | 11/2003 | Chun | A61L 27/34 264/339 |
| 2003/0212431 A1 | 11/2003 | Brady et al. | |
| 2003/0220683 A1 | 11/2003 | Minasian et al. | |
| 2003/0225445 A1 | 12/2003 | Derus | |
| 2003/0225446 A1 | 12/2003 | Hartley | |
| 2003/0225449 A1 | 12/2003 | Denison | |
| 2003/0236443 A1 | 12/2003 | Cespedes | |
| 2003/0236568 A1 | 12/2003 | Hojeibane et al. | |
| 2004/0006380 A1 | 1/2004 | Buck et al. | |
| 2004/0015230 A1 | 1/2004 | Moll | |
| 2004/0015232 A1 | 1/2004 | Salazar | |
| 2004/0019374 A1 | 1/2004 | Hojeibane et al. | |
| 2004/0024444 A1 | 2/2004 | Moore | |
| 2004/0024447 A1 | 2/2004 | Haverich | |
| 2004/0024452 A1 | 2/2004 | Kruse et al. | |
| 2004/0029993 A1 | 2/2004 | Klee et al. | |
| 2004/0034409 A1 | 2/2004 | Heublein et al. | |
| 2004/0044401 A1 | 3/2004 | Bales et al. | |
| 2004/0044407 A1 | 3/2004 | Verona | |
| 2004/0047909 A1 | 3/2004 | Ragheb | |
| 2004/0049262 A1 | 3/2004 | Obermiller et al. | |
| 2004/0049266 A1 | 3/2004 | Anduiza et al. | |
| 2004/0059411 A1 | 3/2004 | Strecker | |
| 2004/0064067 A1 | 4/2004 | Ward | |
| 2004/0073155 A1 | 4/2004 | Laufer et al. | |
| 2004/0073230 A1 | 4/2004 | Mulholland et al. | |
| 2004/0073238 A1 | 4/2004 | Makower | |
| 2004/0073242 A1 | 4/2004 | Chanduszko | |
| 2004/0073297 A1 | 4/2004 | Rohde et al. | |
| 2004/0078053 A1 | 4/2004 | Berg et al. | |
| 2004/0093017 A1 | 5/2004 | Chanduszko | |
| 2004/0093061 A1 | 5/2004 | Acosta et al. | |
| 2004/0093070 A1 | 5/2004 | Hojeibane et al. | |
| 2004/0093073 A1 | 5/2004 | Lowe et al. | |
| 2004/0098030 A1 | 5/2004 | Makower et al. | |
| 2004/0098079 A1 | 5/2004 | Hartley | |
| 2004/0098098 A1 | 5/2004 | McGucking et al. | |
| 2004/0102806 A1 | 5/2004 | Broome et al. | |
| 2004/0102834 A1 | 5/2004 | Nakano et al. | |
| 2004/0102855 A1 | 5/2004 | Shank | |
| 2004/0106985 A1 | 6/2004 | Jang | |
| 2004/0111145 A1 | 6/2004 | Serino et al. | |
| 2004/0117004 A1 | 6/2004 | Osborne et al. | |
| 2004/0117010 A1 | 6/2004 | Houston et al. | |
| 2004/0117031 A1 | 6/2004 | Stack et al. | |
| 2004/0122448 A1 | 6/2004 | Levine | |
| 2004/0127981 A1 | 7/2004 | Rahdert et al. | |
| 2004/0127982 A1 | 7/2004 | Machold et al. | |
| 2004/0137042 A1 | 7/2004 | Hiles et al. | |
| 2004/0138737 A1 | 7/2004 | Davidson et al. | |

(56) References Cited

U.S. PATENT DOCUMENTS

| | | |
|---|---|---|
| 2004/0143277 A1 | 7/2004 | Marino et al. |
| 2004/0143291 A1 | 7/2004 | Corcoran et al. |
| 2004/0143292 A1 | 7/2004 | Marino et al. |
| 2004/0143293 A1 | 7/2004 | Marino et al. |
| 2004/0143294 A1 | 7/2004 | Corcoran et al. |
| 2004/0148000 A1 | 7/2004 | Bilge |
| 2004/0158331 A1 | 8/2004 | Stack et al. |
| 2004/0166169 A1 | 8/2004 | Malaviya et al. |
| 2004/0167566 A1 | 8/2004 | Beulke et al. |
| 2004/0167619 A1 | 8/2004 | Case et al. |
| 2004/0080352 A1 | 9/2004 | Bleyer |
| 2004/0172141 A1 | 9/2004 | Stack et al. |
| 2004/0176799 A1 | 9/2004 | Chanduszko et al. |
| 2004/0180042 A1 | 9/2004 | Cook et al. |
| 2004/0186558 A1 | 9/2004 | Pavcnik |
| 2004/0210301 A1 | 10/2004 | Obermiller |
| 2004/0210306 A1 | 10/2004 | Quijano et al. |
| 2004/0213756 A1 | 10/2004 | Michal et al. |
| 2004/0215333 A1 | 10/2004 | Duran et al. |
| 2004/0220610 A1 | 11/2004 | Kreidler et al. |
| 2004/0224868 A1 | 11/2004 | Meyerhoff et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225356 A1 | 11/2004 | Frater |
| 2004/0230222 A1 | 11/2004 | Van der Burg et al. |
| 2004/0230287 A1 | 11/2004 | Hartley |
| 2004/0243216 A1 | 12/2004 | Gregorich |
| 2004/0243218 A1 | 12/2004 | Schaeffer |
| 2004/0243219 A1 | 12/2004 | Fischer et al. |
| 2004/0243222 A1 | 12/2004 | Osborne et al. |
| 2004/0249439 A1 | 12/2004 | Richter et al. |
| 2004/0254640 A1 | 12/2004 | Sutherland et al. |
| 2004/0260229 A1 | 12/2004 | Meir |
| 2004/0260328 A1 | 12/2004 | Zvuloni et al. |
| 2004/0260340 A1 | 12/2004 | Jacobs et al. |
| 2004/0260389 A1 | 12/2004 | Case |
| 2004/0260393 A1 | 12/2004 | Rahdert et al. |
| 2004/0267191 A1 | 12/2004 | Gifford, III et al. |
| 2004/0267306 A1 | 12/2004 | Blaeser et al. |
| 2005/0004659 A1 | 1/2005 | Von Oepen et al. |
| 2005/0010248 A1 | 1/2005 | Lafontaine |
| 2005/0010285 A1 | 1/2005 | Lambrecht et al. |
| 2005/0010287 A1 | 1/2005 | Macoviak et al. |
| 2005/0033398 A1 | 2/2005 | Seguin |
| 2005/0034735 A1 | 2/2005 | Deem et al. |
| 2005/0038501 A1 | 2/2005 | Moore, Jr. et al. |
| 2005/0043708 A1 | 2/2005 | Gleeson et al. |
| 2005/0043759 A1 | 2/2005 | Chanduszko |
| 2005/0049634 A1 | 3/2005 | Chopra |
| 2005/0055079 A1 | 3/2005 | Duran et al. |
| 2005/0059923 A1 | 3/2005 | Gamboa |
| 2005/0060024 A1 | 3/2005 | Lee et al. |
| 2005/0065547 A1 | 3/2005 | Marino et al. |
| 2005/0065548 A1 | 3/2005 | Marino et al. |
| 2005/0065614 A1 | 3/2005 | Stinson |
| 2005/0070794 A1 | 3/2005 | Deal et al. |
| 2005/0070821 A1 | 3/2005 | Deal et al. |
| 2005/0075713 A1 | 4/2005 | Biancucci et al. |
| 2005/0075725 A1 | 4/2005 | Rowe |
| 2005/0075726 A1 | 4/2005 | Svanidze et al. |
| 2005/0075728 A1 | 4/2005 | Nguyen et al. |
| 2005/0085843 A1 | 4/2005 | Opolski et al. |
| 2005/0085900 A1 | 4/2005 | Case et al. |
| 2005/0092335 A1 | 5/2005 | Bertrand |
| 2005/0096734 A1 | 5/2005 | Majercak et al. |
| 2005/0096735 A1 | 5/2005 | Hojeibane et al. |
| 2005/0096736 A1 | 5/2005 | Case |
| 2005/0113686 A1 | 5/2005 | Peckham et al. |
| 2005/0113910 A1 | 5/2005 | Paniagua |
| 2005/0125032 A1 | 6/2005 | Whisenant et al. |
| 2005/0125050 A1 | 6/2005 | Carter |
| 2005/0137676 A1 | 6/2005 | Richardson et al. |
| 2005/0137681 A1 | 6/2005 | Shoemaker et al. |
| 2005/0143801 A1 | 6/2005 | Aboul-Hosn |
| 2005/0143806 A1 | 6/2005 | Phillips |
| 2005/0143807 A1 | 6/2005 | Pavcnik |
| 2005/0149459 A1 | 7/2005 | Andreas et al. |
| 2005/0154405 A1 | 7/2005 | Kraemer et al. |
| 2005/0163818 A1 | 7/2005 | Sung et al. |
| 2005/0171592 A1 | 8/2005 | Majercak |
| 2005/0182483 A1 | 8/2005 | Osborne et al. |
| 2005/0187565 A1 | 8/2005 | Baker et al. |
| 2005/0187614 A1 | 8/2005 | Agnew |
| 2005/0191496 A1 | 9/2005 | Maschke |
| 2005/0192626 A1 | 9/2005 | Widomski et al. |
| 2005/0192627 A1 | 9/2005 | Whisenant et al. |
| 2005/0203568 A1 | 9/2005 | Burg et al. |
| 2005/0216077 A1 | 9/2005 | Mathis et al. |
| 2005/0222661 A1 | 10/2005 | Case et al. |
| 2005/0228434 A1 | 10/2005 | Amplatz et al. |
| 2005/0228479 A1 | 10/2005 | Pavcnik et al. |
| 2005/0228486 A1 | 10/2005 | Case |
| 2005/0228495 A1 | 10/2005 | Macoviak |
| 2005/0228505 A1 | 10/2005 | Cornet et al. |
| 2005/0234509 A1 | 10/2005 | Widomski et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240255 A1 | 10/2005 | Schaeffer |
| 2005/0249772 A1 | 11/2005 | Malaviya et al. |
| 2005/0251201 A1 | 11/2005 | Roue et al. |
| 2005/0256532 A1 | 11/2005 | Nayak et al. |
| 2005/0261759 A1 | 11/2005 | Lambrecht et al. |
| 2005/0267524 A1 | 12/2005 | Chanduszko |
| 2005/0267526 A1 | 12/2005 | Wahr et al. |
| 2005/0267560 A1 | 12/2005 | Bates |
| 2005/0267573 A9 | 12/2005 | Macoviak et al. |
| 2005/0273124 A1 | 12/2005 | Chanduszko |
| 2005/0273153 A1 | 12/2005 | Clerc et al. |
| 2005/0273160 A1 | 12/2005 | Lashinski et al. |
| 2005/0283187 A1 | 12/2005 | Longson |
| 2005/0288706 A1 | 12/2005 | Widomski et al. |
| 2005/0288786 A1 | 12/2005 | Chanduszko |
| 2006/0004433 A1 | 1/2006 | Greenberg |
| 2006/0004436 A1 | 1/2006 | Amarant et al. |
| 2006/0009800 A1 | 1/2006 | Christianson et al. |
| 2006/0015178 A1 | 1/2006 | Moaddeb et al. |
| 2006/0020332 A1 | 1/2006 | Lashinski et al. |
| 2006/0020334 A1 | 1/2006 | Lashinski et al. |
| 2006/0025844 A1 | 2/2006 | Majercak et al. |
| 2006/0030923 A1 | 2/2006 | Gunderson |
| 2006/0036282 A1 | 2/2006 | Wahr et al. |
| 2006/0041302 A1 | 2/2006 | Malewicz |
| 2006/0041319 A1 | 2/2006 | Taylor et al. |
| 2006/0047338 A1 | 3/2006 | Jenson et al. |
| 2006/0052816 A1 | 3/2006 | Bates et al. |
| 2006/0052821 A1 | 3/2006 | Abbott et al. |
| 2006/0058865 A1 | 3/2006 | Case et al. |
| 2006/0058889 A1 | 3/2006 | Case et al. |
| 2006/0064152 A1 | 3/2006 | Olson |
| 2006/0069430 A9 | 3/2006 | Rahdert et al. |
| 2006/0074352 A1 | 4/2006 | Case et al. |
| 2006/0074480 A1 | 4/2006 | Bales et al. |
| 2006/0089708 A1 | 4/2006 | Osse et al. |
| 2006/0100531 A1 | 5/2006 | Moser |
| 2006/0106418 A1 | 5/2006 | Seibold et al. |
| 2006/0106420 A1 | 5/2006 | Dolan et al. |
| 2006/0106454 A1 | 5/2006 | Osborne |
| 2006/0106456 A9 | 5/2006 | Machold et al. |
| 2006/0111770 A1 | 5/2006 | Pavcnik et al. |
| 2006/0111773 A1 | 5/2006 | Rittgers et al. |
| 2006/0116548 A1 | 6/2006 | Case et al. |
| 2006/0116572 A1 | 6/2006 | Case |
| 2006/0122646 A1 | 6/2006 | Corcoran et al. |
| 2006/0136044 A1 | 6/2006 | Osborne et al. |
| 2006/0136045 A1 | 6/2006 | Flagle et al. |
| 2006/0155327 A1 | 7/2006 | Briganti et al. |
| 2006/0167468 A1 | 7/2006 | Gabbay |
| 2006/0173532 A1 | 8/2006 | Flagle et al. |
| 2006/0178729 A1 | 8/2006 | Thielen et al. |
| 2006/0178730 A1 | 8/2006 | Hill et al. |
| 2006/0178740 A1 | 8/2006 | Stacchino et al. |
| 2006/0184239 A1 | 8/2006 | Andrieu et al. |

(56) References Cited

U.S. PATENT DOCUMENTS

| | | |
|---|---|---|
| 2006/0195004 A1 | 8/2006 | Jarvik |
| 2006/0200196 A1 | 9/2006 | Zang et al. |
| 2006/0201996 A1 | 9/2006 | Hodde |
| 2006/0210597 A1 | 9/2006 | Hiles |
| 2006/0210603 A1 | 9/2006 | Williams et al. |
| 2006/0212107 A1 | 9/2006 | Case et al. |
| 2006/0212110 A1 | 9/2006 | Osborne et al. |
| 2006/0212111 A1 | 9/2006 | Case et al. |
| 2006/0216326 A1 | 9/2006 | Pacetti |
| 2006/0217760 A1 | 9/2006 | Widomski et al. |
| 2006/0217761 A1 | 9/2006 | Opolski |
| 2006/0229670 A1 | 10/2006 | Bates |
| 2006/0229702 A1 | 10/2006 | Agnew |
| 2006/0230592 A1 | 10/2006 | Heaney |
| 2006/0235467 A1 | 10/2006 | DeVore |
| 2006/0235511 A1 | 10/2006 | Osborne |
| 2006/0241675 A1 | 10/2006 | Johnson et al. |
| 2006/0241744 A1 | 10/2006 | Beith |
| 2006/0247762 A1 | 11/2006 | Acosta et al. |
| 2006/0253188 A1 | 11/2006 | Case |
| 2006/0259115 A1 | 11/2006 | Case et al. |
| 2006/0259128 A1 | 11/2006 | Pavcnik et al. |
| 2006/0259136 A1 | 11/2006 | Nguyen |
| 2006/0265053 A1 | 11/2006 | Hunt |
| 2006/0271030 A1 | 11/2006 | Francis et al. |
| 2006/0271159 A1 | 11/2006 | Gregorich et al. |
| 2006/0276813 A1 | 12/2006 | Greenberg |
| 2006/0276882 A1* | 12/2006 | Case .................. A61F 2/07 623/1.24 |
| 2006/0282157 A1 | 12/2006 | Hill et al. |
| 2006/0287717 A1 | 12/2006 | Rowe et al. |
| 2007/0016306 A1 | 1/2007 | Dua et al. |
| 2007/0021826 A1 | 1/2007 | Case |
| 2007/0027460 A1 | 2/2007 | Case et al. |
| 2007/0027535 A1 | 2/2007 | Purdy et al. |
| 2007/0027549 A1 | 2/2007 | Godin |
| 2007/0038291 A1 | 2/2007 | Case |
| 2007/0043431 A1 | 2/2007 | Melsheimer |
| 2007/0056346 A1 | 3/2007 | Spenser |
| 2007/0061002 A1 | 3/2007 | Paul, Jr. et al. |
| 2007/0061009 A1 | 3/2007 | Spenser |
| 2007/0088424 A1 | 4/2007 | Greenberg |
| 2007/0093887 A1 | 4/2007 | Case et al. |
| 2007/0100435 A1 | 5/2007 | Case |
| 2007/0106372 A1 | 5/2007 | Osborne et al. |
| 2007/0112423 A1 | 5/2007 | Chu |
| 2007/0112437 A1 | 5/2007 | Shank |
| 2007/0129738 A1 | 6/2007 | Kraemer et al. |
| 2007/0135826 A1 | 6/2007 | Zaver et al. |
| 2007/0162057 A1 | 7/2007 | Kraemer et al. |
| 2007/0162058 A1 | 7/2007 | Kraemer et al. |
| 2007/0162103 A1 | 7/2007 | Case |
| 2007/0167961 A1 | 7/2007 | Kraemer et al. |
| 2007/0173919 A1 | 7/2007 | Maschke |
| 2007/0185560 A1 | 8/2007 | Roeder et al. |
| 2007/0185565 A1 | 8/2007 | Schwammenthal et al. |
| 2007/0208429 A1 | 9/2007 | Leahy |
| 2007/0213813 A1 | 9/2007 | Segesser et al. |
| 2007/0225798 A1 | 9/2007 | Gregorich |
| 2007/0227518 A1 | 10/2007 | Case |
| 2007/0233237 A1 | 10/2007 | Krivoruchko |
| 2007/0239273 A1 | 10/2007 | Allen |
| 2007/0244545 A1 | 10/2007 | Birdsall et al. |
| 2007/0260263 A1 | 11/2007 | Case et al. |
| 2007/0260327 A1 | 11/2007 | Case et al. |
| 2007/0270931 A1 | 11/2007 | Leanna |
| 2007/0270932 A1 | 11/2007 | Headley |
| 2007/0270937 A1 | 11/2007 | Leanna |
| 2007/0288086 A1 | 12/2007 | Kalmann et al. |
| 2007/0288087 A1 | 12/2007 | Gabbay |
| 2008/0009934 A1 | 1/2008 | Schneider |
| 2008/0046071 A1 | 2/2008 | Pavcnik |
| 2008/0051879 A1 | 2/2008 | Case et al. |
| 2008/0082166 A1 | 4/2008 | Styrc et al. |
| 2008/0091235 A1 | 4/2008 | Sirota |
| 2008/0103582 A1 | 5/2008 | Randall et al. |
| 2008/0125860 A1 | 5/2008 | Webler et al. |
| 2008/0140110 A1 | 6/2008 | Spence |
| 2008/0200936 A1 | 8/2008 | Kraemer et al. |
| 2008/0200937 A1 | 8/2008 | Kraemer et al. |
| 2008/0208215 A1 | 8/2008 | Kraemer et al. |
| 2008/0221656 A1 | 9/2008 | Hartley |
| 2008/0228206 A1 | 9/2008 | Kraemer et al. |
| 2008/0228285 A1 | 9/2008 | Kraemer et al. |
| 2008/0243246 A1 | 10/2008 | Ryan et al. |
| 2008/0249538 A1 | 10/2008 | Kraemer et al. |
| 2008/0249609 A1 | 10/2008 | Shanley |
| 2008/0249612 A1 | 10/2008 | Osborne et al. |
| 2008/0249619 A1 | 10/2008 | Stacchino et al. |
| 2008/0275470 A1 | 11/2008 | Kraemer et al. |
| 2008/0281337 A1 | 11/2008 | Kraemer et al. |
| 2008/0287966 A1 | 11/2008 | Kraemer et al. |
| 2008/0312735 A1 | 12/2008 | Thorpe et al. |
| 2009/0005863 A1 | 1/2009 | Goetz et al. |
| 2009/0018649 A1 | 1/2009 | Jaffe et al. |
| 2009/0062836 A1 | 3/2009 | Kurrus |
| 2009/0062844 A1 | 3/2009 | Tekulve |
| 2009/0082858 A1 | 3/2009 | Nugent et al. |
| 2009/0088836 A1 | 4/2009 | Bishop et al. |
| 2009/0099653 A1 | 4/2009 | Suri et al. |
| 2009/0105813 A1* | 4/2009 | Chambers .............. A61F 2/2412 623/2.12 |
| 2009/0118712 A1 | 5/2009 | Carter et al. |
| 2009/0132037 A1* | 5/2009 | Hoffman .............. A61F 2/2418 623/2.38 |
| 2009/0177275 A1 | 7/2009 | Case |
| 2009/0216321 A1 | 8/2009 | Osborne et al. |
| 2009/0234434 A1 | 9/2009 | Johnson et al. |
| 2009/0240320 A1 | 9/2009 | Tuval et al. |
| 2009/0248132 A1 | 10/2009 | Bloom et al. |
| 2009/0264991 A1 | 10/2009 | Paul et al. |
| 2009/0270965 A1 | 10/2009 | Sinha et al. |
| 2009/0287300 A1 | 11/2009 | Dave et al. |
| 2009/0292350 A1* | 11/2009 | Eberhardt ............ A61F 2/2418 623/1.16 |
| 2010/0023114 A1 | 1/2010 | Chambers et al. |
| 2010/0030246 A1 | 2/2010 | Pavcnik et al. |
| 2010/0030259 A1 | 2/2010 | Pavcnik et al. |
| 2010/0030314 A1 | 2/2010 | Case et al. |
| 2010/0036484 A1* | 2/2010 | Hariton ................ A61F 2/2412 623/2.18 |
| 2010/0057191 A1 | 3/2010 | Pavcnik et al. |
| 2010/0063577 A1 | 3/2010 | Case et al. |
| 2010/0114296 A1 | 5/2010 | Case et al. |
| 2010/0114300 A1 | 5/2010 | Case et al. |
| 2010/0121461 A1 | 5/2010 | Sobrino-Serrano et al. |
| 2010/0121462 A1 | 5/2010 | Sobrino-Serrano et al. |
| 2010/0131055 A1 | 5/2010 | Case et al. |
| 2010/0137998 A1 | 6/2010 | Sobrino-Serrano et al. |
| 2010/0174364 A1* | 7/2010 | Hoffman .............. A61F 2/2412 623/2.17 |
| 2010/0185277 A1* | 7/2010 | Braido ................ A61F 2/2433 623/2.18 |
| 2011/0054497 A1 | 3/2011 | Kraemer et al. |
| 2011/0087198 A1 | 4/2011 | Carter et al. |
| 2011/0087337 A1 | 4/2011 | Forsell |
| 2011/0098800 A1* | 4/2011 | Braido ................ A61F 2/2418 623/1.16 |
| 2011/0160753 A1 | 6/2011 | Bastin |
| 2011/0190796 A1 | 8/2011 | Kraemer et al. |
| 2011/0190905 A1 | 8/2011 | Behan |
| 2011/0202078 A1 | 8/2011 | Kraemer et al. |
| 2012/0053681 A1* | 3/2012 | Alkhatib .............. A61F 2/2418 623/2.11 |
| 2012/0071969 A1* | 3/2012 | Li ........................ A61F 2/24 623/2.17 |
| 2012/0078347 A1* | 3/2012 | Braido ................ A61F 2/2418 623/1.26 |
| 2012/0089223 A1* | 4/2012 | Nguyen ................ A61F 2/2418 623/2.14 |
| 2012/0130476 A1 | 5/2012 | Paul et al. |
| 2012/0185038 A1* | 7/2012 | Fish ...................... A61F 2/2415 623/2.13 |

(56) References Cited

U.S. PATENT DOCUMENTS

| | | | | |
|---|---|---|---|---|
| 2012/0197390 A1 | * | 8/2012 | Alkhatib | A61F 2/2436 623/2.18 |
| 2012/0203327 A1 | | 8/2012 | Case et al. | |
| 2012/0253446 A1 | | 10/2012 | Osborne et al. | |
| 2012/0253450 A1 | | 10/2012 | Case et al. | |
| 2012/0323306 A1 | | 12/2012 | Case et al. | |
| 2012/0330413 A1 | | 12/2012 | Pavcnik | |
| 2013/0018453 A1 | | 1/2013 | Case et al. | |
| 2013/0079867 A1 | | 3/2013 | Hoffman et al. | |
| 2013/0079868 A1 | | 3/2013 | Agnew | |
| 2013/0110254 A1 | | 5/2013 | Osborne | |
| 2013/0116720 A1 | | 5/2013 | Theobald et al. | |
| 2013/0123768 A1 | | 5/2013 | Harlan | |
| 2013/0150956 A1 | * | 6/2013 | Yohanan | A61F 2/2433 623/2.14 |
| 2013/0226291 A1 | | 8/2013 | Pavcnik et al. | |
| 2013/0289706 A1 | | 10/2013 | Schaeffer et al. | |
| 2014/0000112 A1 | * | 1/2014 | Braido | A61F 2/2418 29/890.12 |
| 2014/0005776 A1 | * | 1/2014 | Braido | A61F 2/2412 623/2.18 |
| 2014/0107691 A1 | | 4/2014 | Lashinski | |
| 2014/0143236 A1 | | 5/2014 | Thompson et al. | |
| 2014/0155987 A1 | | 6/2014 | Paul et al. | |
| 2014/0155997 A1 | * | 6/2014 | Braido | A61F 2/2433 623/2.37 |
| 2014/0163667 A1 | | 6/2014 | Lashinski et al. | |
| 2014/0228937 A1 | | 8/2014 | Krieger et al. | |
| 2015/0230923 A1 | * | 8/2015 | Levi | A61F 2/2418 623/2.36 |
| 2016/0067031 A1 | * | 3/2016 | Kassab | A61L 27/3804 424/569 |
| 2016/0175095 A1 | * | 6/2016 | Dienno | A61F 2/2415 623/2.17 |
| 2017/0128212 A1 | * | 5/2017 | Chambers | A61F 2/2418 |

FOREIGN PATENT DOCUMENTS

| | | |
|---|---|---|
| AU | 2004220576 | 9/2004 |
| CA | 2381787 | 3/2001 |
| CA | 2401996 | 3/2001 |
| CA | 2403030 | 9/2002 |
| CA | 2518867 | 9/2004 |
| CA | 2523262 | 11/2004 |
| DE | 2246526 | 3/1973 |
| DE | 19851846 | 5/2000 |
| DE | 10223399 | 12/2003 |
| EP | 103546 | 3/1984 |
| EP | 0350302 | 1/1990 |
| EP | 0357003 | 3/1990 |
| EP | 0386936 | 9/1990 |
| EP | 0520126 | 11/1991 |
| EP | 0460428 | 12/1991 |
| EP | 0493788 | 7/1992 |
| EP | 0592410 | 4/1994 |
| EP | 0657147 | 6/1995 |
| EP | 0732089 | 9/1996 |
| EP | 0800801 | 6/1997 |
| EP | 0792627 | 9/1997 |
| EP | 0808614 | 11/1997 |
| EP | 0850607 | 7/1998 |
| EP | 0938880 | 9/1999 |
| EP | 1057460 | 12/2000 |
| EP | 1179321 | 2/2002 |
| EP | 1230901 | 8/2002 |
| EP | 1362563 | 11/2003 |
| EP | 1472996 | 4/2004 |
| EP | 1615595 | 4/2004 |
| EP | 1579886 | 9/2005 |
| EP | 1434538 | 1/2007 |
| EP | 1626681 | 7/2009 |
| EP | 1603492 | 12/2009 |
| EP | 1615593 | 1/2010 |
| EP | 2163224 | 3/2010 |
| EP | 2201911 | 6/2010 |
| EP | 1229865 | 11/2010 |
| EP | 2120795 | 7/2011 |
| EP | 2222247 | 8/2012 |
| EP | 1887980 | 9/2012 |
| EP | 1928512 | 11/2012 |
| EP | 1659992 | 3/2013 |
| FR | 2722678 | 7/1994 |
| FR | 2785174 | 5/2000 |
| FR | 2788217 | 7/2000 |
| FR | 2828091 | 2/2003 |
| GB | 1598111 | 4/1977 |
| GB | 2056023 | 3/1981 |
| GB | 0386936 | 8/2004 |
| JP | S61137556 | 6/1986 |
| JP | S62-227352 | 10/1987 |
| JP | 02-307480 | 12/1990 |
| JP | 4383707 | 10/2009 |
| JP | 4589395 | 12/2010 |
| JP | 4624984 | 12/2010 |
| JP | 4940388 | 3/2012 |
| SU | 1258406 | 9/1986 |
| SU | 1271508 | 11/1986 |
| SU | 1371701 | 2/1988 |
| WO | WO8302225 | 7/1983 |
| WO | WO8501651 | 4/1985 |
| WO | WO9014804 | 12/1990 |
| WO | WO9117720 | 11/1991 |
| WO | WO9209247 | 11/1991 |
| WO | WO9217118 | 10/1992 |
| WO | WO9407560 | 4/1994 |
| WO | WO9527448 | 10/1995 |
| WO | WO9637167 | 11/1996 |
| WO | WO9640008 | 12/1996 |
| WO | WO9640011 | 12/1996 |
| WO | WO9724082 | 7/1997 |
| WO | WO9725937 | 7/1997 |
| WO | WO9728744 | 8/1997 |
| WO | WO9732543 | 9/1997 |
| WO | WO9819732 | 11/1997 |
| WO | WO9822045 | 5/1998 |
| WO | WO9825636 | 6/1998 |
| WO | WO9825637 | 6/1998 |
| WO | WO9826291 | 6/1998 |
| WO | WO9827868 | 7/1998 |
| WO | WO9846165 | 10/1998 |
| WO | WO9858600 | 12/1998 |
| WO | WO9915224 | 4/1999 |
| WO | WO9933414 | 7/1999 |
| WO | WO9959503 | 11/1999 |
| WO | WO9962431 | 12/1999 |
| WO | WO0040176 | 7/2000 |
| WO | WO0042950 | 7/2000 |
| WO | WO0047134 | 8/2000 |
| WO | 0067679 | 11/2000 |
| WO | WO0064380 | 11/2000 |
| WO | WO0067661 | 11/2000 |
| WO | WO0112105 | 2/2001 |
| WO | 0119285 | 3/2001 |
| WO | WO0128459 | 4/2001 |
| WO | WO0130275 | 5/2001 |
| WO | WO0149213 | 7/2001 |
| WO | WO0154625 | 8/2001 |
| WO | WO0156500 | 8/2001 |
| WO | WO0166035 | 9/2001 |
| WO | WO0166037 | 9/2001 |
| WO | WO0166043 | 9/2001 |
| WO | WO0166190 | 9/2001 |
| WO | WO0174273 | 10/2001 |
| WO | WO200183017 | 11/2001 |
| WO | WO0207601 | 1/2002 |
| WO | WO2002024119 | 3/2002 |
| WO | WO0236045 | 5/2002 |
| WO | WO0239888 | 5/2002 |
| WO | WO0241764 | 5/2002 |
| WO | WO0243620 | 6/2002 |
| WO | WO0249541 | 6/2002 |
| WO | WO02102284 | 12/2002 |
| WO | WO03002165 | 1/2003 |

(56) References Cited

FOREIGN PATENT DOCUMENTS

| WO | WO03011195 | 2/2003 |
|---|---|---|
| WO | WO03030776 | 4/2003 |
| WO | WO03030782 | 4/2003 |
| WO | WO03047468 | 6/2003 |
| WO | WO03063733 | 8/2003 |
| WO | WO03088872 | 10/2003 |
| WO | WO03101346 | 12/2003 |
| WO | WO2003101346 | 12/2003 |
| WO | WO2004016200 | 2/2004 |
| WO | WO2004016201 | 2/2004 |
| WO | WO2004045703 | 6/2004 |
| WO | WO2004080352 | 9/2004 |
| WO | WO2004082528 | 9/2004 |
| WO | WO2004082530 | 9/2004 |
| WO | WO2004089253 | 10/2004 |
| WO | WO2004091449 | 10/2004 |
| WO | 2004096100 | 11/2004 |
| WO | WO2004093745 | 11/2004 |
| WO | WO2004103222 | 12/2004 |
| WO | WO2004105651 | 12/2004 |
| WO | WO2005011535 | 2/2005 |
| WO | WO2005020612 | 3/2005 |
| WO | WO05062931 | 7/2005 |
| WO | WO2005082289 | 9/2005 |
| WO | WO2005099623 | 10/2005 |
| WO | WO2005099628 | 10/2005 |
| WO | WO2006026325 | 3/2006 |
| WO | WO2006028821 | 3/2006 |
| WO | WO2006031436 | 3/2006 |
| WO | 2006050460 | 5/2006 |
| WO | WO2006071245 | 7/2006 |
| WO | WO2006124647 | 11/2006 |
| WO | WO2006125055 | 11/2006 |
| WO | WO2007047945 | 4/2007 |
| WO | WO2007061801 | 5/2007 |
| WO | WO2007092274 | 8/2007 |
| WO | WO07108857 | 9/2007 |
| WO | 2007123658 | 11/2007 |
| WO | WO2007130614 | 11/2007 |
| WO | WO2007139677 | 12/2007 |
| WO | WO2007142935 | 12/2007 |
| WO | WO2008073582 | 6/2008 |
| WO | WO2008094706 | 8/2008 |
| WO | WO2008101083 | 8/2008 |
| WO | WO08150529 | 12/2008 |
| WO | WO2009052340 | 4/2009 |
| WO | WO2009073774 | 6/2009 |
| WO | WO2009088957 | 7/2009 |
| WO | WO2009129481 | 10/2009 |
| WO | WO2010042950 | 4/2010 |
| WO | WO2010080884 | 7/2010 |
| WO | WO2010091188 | 8/2010 |
| WO | WO2010099209 | 9/2010 |
| WO | WO2011109450 | 9/2011 |
| WO | WO2012051489 | 4/2012 |
| WO | WO2013120082 | 8/2013 |
| WO | WO03092554 | 11/2013 |
| WO | WO2014124356 | 8/2014 |

OTHER PUBLICATIONS

Bai, Yuan, et al., "Percutaneous establishment of tricuspid regugitation: an experimental model for transcatheter tricuspid valve replacement," Chin. Med. J. 2010; 123(7), pp. 806-809.

Lamba, et al., "Degradation of Polyurethanes," Polyurethanes in Biomedical Applications, 181-204, 1998.

Matthias Chiquet, "Regulation of extracellular matrix gene expression by mechanical stress," Matrix Biol., 417-426, 1999.

Marcy Wong, Mark Siegrist, Xuesong Cao, "Cyclic compression of articular cartilage explants is associated with progressive consolidation and altered expression pattern of extracellular matrix proteins," Matrix Biology, 391-399, 1999.

Alan J. Grodzinsky, Marc E. Levenston, Moonsoo Jin, Eliot H. Frank, "Cartilage Tissue Remodeling in Response to Mechanical Forces," Annual Review of Biomedical Engineering, 691-713, 2000.

V.C. Mudera, R. Pleass, M. Eastwood, R. Tarnuzzer, G. Schultz, P. Khaw, D.A. Mcgrouther, R.A. Brown, "Molecular Responses of Human Dermal Fibroblasts to Dual Cues: Contact Guidance and Mechanical Load," Cell Motility and the Cytoskeleton, 45: 1-9, 2000.

Christof Schild, Beat Trueb, "Mechanical Stress is Required for High-Level Expression of Connective Tissue Growth Factor," Experimental Cell Research, 274: 83-91, 2002.

Heeschen, Christopher, et al., "Nicotine Stimulates Angiogensis and Promotes Tumor Growth and Atherosclerosis", Nature Medicine vol. 7, No. 7, (Jul. 2001), pp. 833-839.

Johnson, Chad, et al., "Matrix Metalloproteinase-9 is Required for Adequate Angiogenic Revascularization of Ischemic Tissues", Circulation Research, Feb. 6, 2004, No. 94, pp. 262-268.

Jux, Christian, et al., "A New Biological Matrix for Septal Occlusion", Journal of Interventional Cardiology, vol. 16, No. 2, (2003), pp. 149-152.

King, Terry D., et al., "Secundum Atrial Septal Defect-Nonoperative Closure During Cardiac Catheterization", JAMA, vol. 235, No. 23, Jun. 7, 1978, pp. 2506-2509.

Mullen, Michael J., et al., "BioSTAR Evaluation STudy (BEST) A Prospective, Multicenter, Phase I Clinic Trial to Evaluate the Feasibility, Efficacy, and Safety of the BioSTAR Bioabsorbable Septal Repair Implant for the Closure of Atrial-Level Shunts", Circulation, Oct. 31, 2006, pp. 19621967.

Oguchi, M., et al., "Mucosa-adhesive water-soluble polymer film for treatment of acute radiation-induced oral mucositis", International Journal of Radiation Oncology Biology Physics, Mar. 15, 1998, vol. 40, No. 5, p. 1033-1037.

Pavcnik, Dusan et al., "Monodisk: Device for Percutaneous Transcatheter Closure of Cardiac Septal Defects", Cardiovasc Intervent Radio (1993) vol. 16, pp. 308-312.

Rashkind, William J., "Transcatheter Treatment of Congenital Heart Disease", Circulation vol. 67, No. 4, Apr. 1983, pp. 711-716.

Sideris, E.B. et al., "Transvenous Atrial Septal Defect Occlusion in Piglets with a 'Buttoned' Double-Disk Device", Circulation, vol. 81, No. 1, Jan. 1990, pp. 312-318.

Jux, Christian, et al., "Interventional Atrial Septal Defect Closure Using a Totally Bioresorbable Occluder Matrix", JACC, vol. 48, No. 1 (2006), pp. 161-169.

Babic, Uros U., et al., "Transcatheter Closure of Atrial Septal Defects", The Lancet, Sep. 1, 1990, pp. 566-567.

Bhattathiri, VN, et al., "Influence of plasma GSH level on acute radiation mucositis of the oral cavity", International Journal of Radiation Oncology Biology Physics (1994), vol. 29, No. 2, pp. 383-386.

Braun, M., et al., "Transcatheter Closure of Patent Foramen Ovale (PFO) in Patients With Paradoxical Embolism", European Heart Journal (2004), vol. 25, pp. 424-430.

Das, Gladwin S., et al., "Experimental Atrial Septal Defect Closure With a New, Transcatheter, Self-Centering Device", Circulation, vol. 88, No. 4, Part 1, Oct. 1993, pp. 1754-1764.

Lurie, Fedor Mechanism of Venous Valve Closure and Role of the Valve in Circulation: A New Concept, J Vasc Surg 2003;38:955-61. Elsevier, Amsterdam, The Netherlands.

Lurie, Fedor, The Mechanism of Venous Valve Closure in Normal Physiologic Conditions, J Vasc Surg 2002;35:713-17. Elsevier, Amsterdam, The Netherlands.

Van Bemmelen, Paul S. and Fedor Lurie, Letters to the Editor, Regarding "The Mechanism of Venous Valve Closure in Normal Physiological Conditions", J Vasc Surg 2003; 37(1) 237-38. Elsevier, Amsterdam, The Netherlands.

Garcia-Rinaldi, Raul, Implantation of Cryopreserved Allograft Pulmonary Monocusp Patch, Tex Heart Inst J 2002;29:92-99. Texas Heart Institute, Houston, TX, USA.

Garcia-Rinaldi, Raul, Femoral Vein Valve Incompetence: Treatment with a Xenograft Monocusp Patch, J Vasc Surg 1986; 932-35. Elsevier, Amsterdam, The Netherlands.

(56) References Cited

OTHER PUBLICATIONS

Dana E. Perrin, James P. English, "Polycaprolactone," Handbook of Bioabsorbable Polymers, 1997, 63-76.
Yuan et al. Geometrical Design and Finite Element Analysis on the Bioprosthetic Heart Valve. International Journal of Innovative Computing, Information and Control. vol. 3 No. 5. Oct. 2007. pp. 1289-1299. [abstract].
Yi-Shuan Li, John Y.-J Shyy, Song Li, Jongdae Lee, Bing US, Michael Karin, Shu Chien, "The Ras-JNK Pathway Is Involved in Shear-Induced Gene Expression," Molecular and Cellular Biology, 1996, 5947-5954.
Wai Hung Wong, David J. Mooney, "Synthesis and Properties of Biodegradable Polymers Used as Synthetic Matrices for Tissue Engineering," I synthetic Biodegradable Polymer Scaffolds, 1997, 51-82.
Schneider (Eur.) AG v. Scimed Life Sys., 852 F. Supp. 813 (D. Minn. 1994).
Bergan, John J., et al., "Chronic Venous Disease," N. Engl. J. Med. 2006; 355: 488-98.
Dougal et al., "Stent Design: Implications for Restenosis," Rev. Cardiovasc Med. 3 (suppl. 5), S16-S22 (2002).
Shu Chien, Song Li, John Y-J Shyy, "Effects of Mechanical Forces on Signal Transdution and Gene Expression in Endothelial Cells," Hypertension 31, 162-169, 1998.
Stephen Badylak, Ph.D., M.D., Klod Lokini, Ph.D., Bob Tullius, M.S., Abby Simmons-Byrd, R.V.T., and Robert Morff, PH.D., "Morphologic Study of Small Intestinal Submucosa as a Body Wall Repair Device," Journal of Surgical Research, 103, 190-202 (2002).
Elias Brountzos, Md, Dusan Pavcnik, Md, PhD, Hans A. Timmermans, BFA, Christopher Corless, Md, PhD, Barry T. Uchida, BS, Edith S, Nihsen, BA, Manabu Nakata, Md, PhD, Maria Schoder, Md, John A. Kaufman, Md, Frederick S. Keller, Md, and Josef Rosch, Md, "Remodeling of Suspended Small Intestinal Submucosa Venous Valve: An Experimental Study in Sheep to Assess the Host Cells' Origin," J. Vasc. Interv. Radiol, 2003 14:349-356.
Stephen S. Kim, Satoshi Kaihara, Mark S. Benvenuto, Byung-Soo Kim, David J. Mooney, and Joseph P. Vacanti, "Small Intestinal Submucosa as a Small-Caliber Venous Graft: A Novel Model for Hepatocyte Transplantation on Synthetic Biodegradable Polymer Scaffolds with Direct Access to the Portal Venous System," Journal of Pediatric Surgery, vol. 34, No. 1 (1999) 124-128.
G.E. Sandusky, Jr., S.F. Badylak, R.J. Morff, W.D. Johnson, and G. Lantz, "Histologic Findings After In Vivo Placement of Small Intestine Submucosal Vascular Grafts and Saphenous Vein Grafts in the Carotid Artery in Dogs," American Journal of Pathology, vol. 140, No. 2 1992, 317-324.
D.K. Gilding, A.M. Reed, "Biodegradable polymers for use in surgery—polyglycolic/poly(actic acid) homo- and copolymers: 1," Polymer, 1997, vol. 20, 1459-1464.
D.K. Gilding, "Biodegradable Polymers," Biocompatibility of Clinical Implant Materials, Chap. 9, pp. 209-232, 1981.
Gabriel Helmlinger, Bradford C. Berk, Robert M. Nerem, "Calcium responses of endothelial cell monolayers subjected to pulsatile and steady laminar flow differ," Am. J. Physiol. Cell Physiol., 269: C367-C375, 1995.
Matthias Chiquet, Mark Matthisson, Manuel Koch, Michael Tannheimer, Ruth Chiquet-Ehrismann, "Regulation of extracellular matrix synthesis by mechanical stress," Biochem. Cell Biol. 74, 737-744 (1996).
United States Patent and Trademark Office, Office Action for U.S. Appl. No. 14/377,619, dated Jul. 6, 2015, pp. 1-188.
United States Patent and Trademark Office, Office Action for U.S. Appl. No. 14/377,619, dated Dec. 18, 2015, pp. 1-17.
United States Patent and Trademark Office, Office Action for U.S. Appl. No. 14/377,619, dated Sep. 8, 2016, pp. 1-13.
United States Patent and Trademark Office, Office Action for U.S. Appl. No. 14/377,619, dated Apr. 6, 2017, pp. 1-24.
United States Patent and Trademark Office, Office Action for U.S. Appl. No. 14/377,619, dated Nov. 1, 2017, pp. 1-33.
United States Patent and Trademark Office, Office Action for U.S. Appl. No. 14/377,619, dated Jul. 3, 2018, pp. 1-16.
United States Patent and Trademark Office, Office Action for U.S. Appl. No. 14/377,619, dated Nov. 21, 2018, pp. 1-11.

\* cited by examiner

EXPANDABLE SUPPORT FRAME AND MEDICAL DEVICE

CROSS REFERENCE TO RELATED APPLICATIONS

This application is a continuation of U.S. patent application Ser. No. 14/176,364, filed on Feb. 10, 2014, and which claims the benefit of U.S. Provisional Application No. 61/763,107, filed on Feb. 11, 2013. The entire contents of each of these related applications is incorporated into this disclosure by reference.

FIELD

The disclosure relates generally to the field of implantable medical devices. More particularly, the disclosure relates to intraluminal support frames and medical devices. Particular embodiments relating to intraluminal valve devices and support frames suitable for use in such devices are described in detail.

BACKGROUND

Expandable intraluminal support frames have proven useful in the medical arts. Some expandable support frames are useful without inclusion of any additional elements. Stents, for example, are routinely used in several body lumens as a means for providing support to ailing vessels, such as coronary and non-coronary vessels. In some medical devices, an expandable support frame provides a scaffold onto which one or more additional elements can be attached to achieve a desired function. Occlusion devices, for example, often include a graft or other sheet-like material attached to an expandable support frame.

Constructed in this way, these medical devices can be delivered and deployed intraluminally to substantially block fluid flow through a body vessel. Similarly, some valve devices include a leaflet or leaflets attached to an expandable support frame in a manner that allows the leaflet or leaflets to move between open and closed positions. Constructed in this way, these medical devices can be delivered and deployed intraluminally to regulate fluid flow through a body vessel.

Considering these roles of intraluminal support frames in the medical arts, a need exists for improved frames. Furthermore, for the various types of intraluminal medical devices that include a support frame and one or more additional elements, a need exists for improved frames that improve the effectiveness of the composite device.

Valve devices provide an example. Several researchers have pursued the development of prosthetic valves that are implantable by minimally invasive techniques. Indeed, the art now contains several examples of implantable venous valve devices. Many of these prior art devices include an expandable support frame and an attached graft member that is fashioned into a valve that regulates fluid flow through the device and, ultimately, a body vessel. For example, a graft member can be in the form of a leaflet that is attached to a support frame and movable between first and second positions. In a first position, the valve is open and allows fluid flow to proceed through a vessel in a first direction, and in a second position the valve is closed to prevent fluid flow in a second, opposite direction. Examples of this type of prosthetic valve are described in commonly owned U.S. Pat. No. 6,508,833 to Pavcnik for a MULTIPLE-SIDED INTRALUMINAL MEDICAL DEVICE, which is hereby incorporated by reference in its entirety.

Despite this and other examples, a need remains for improved medical devices, including implantable valve devices, that include an expandable support frame.

BRIEF OVERVIEW OF EXAMPLE EMBODIMENTS

Various example support frames and medical devices are described and illustrated herein.

An example support frame comprises a first circumferential serpentine path; a second circumferential serpentine path; a first connector segment joining the first and second serpentine paths, the first connector segment comprising substantially parallel first and second struts; a second connector segment disposed substantially opposite the first connector segment with respect to the longitudinal axis of the support frame and joining the first and second serpentine paths, the second connector segment comprising substantially parallel third and fourth struts; a third connector segment disposed circumferentially adjacent the first and second connector segments and joining the first and second serpentine paths; a fourth connector segment disposed substantially opposite the third connector segment and joining the first and second serpentine paths; a first connector strut extending between and joining the first and third connector segments; and a second connector strut extending between and joining the second and third connector segments.

An example medical device comprises an expandable support frame having a longitudinal axis, an outer circumference, an unexpanded configuration, and an expanded configuration with an expanded configuration radius extending from the longitudinal axis to the outer circumference; a first leaflet attached to the support frame along a first attachment pathway, the first leaflet having a first inner surface that defines a domed radius equal to or less than the expanded configuration radius when the support frame is in the expanded configuration; and a second leaflet attached to the support frame along a second attachment pathway, the second leaflet having a second inner surface that defines a second domed radius equal to or less than the expanded configuration radius when the support frame is in the expanded configuration.

Another example medical device comprises an expandable support frame having a longitudinal axis, an outer circumference, an unexpanded configuration, and an expanded configuration with an expanded configuration radius extending from the longitudinal axis to the outer circumference. For this example medical device, the expandable support frame comprises a first circumferential serpentine path; a second circumferential serpentine path; a first connector segment joining the first and second serpentine paths, the first connector segment comprising substantially parallel first and second struts; a second connector segment disposed substantially opposite the first connector segment with respect to said longitudinal axis and joining the first and second serpentine paths, the second connector segment comprising substantially parallel third and fourth struts; a third connector segment disposed circumferentially adjacent the first and second connector segments and joining the first and second serpentine paths; a fourth connector segment disposed substantially opposite the third connector segment and joining the first and second serpentine paths; a first connector strut extending between and joining the first and third connector segments; and a second connector strut extending between and joining the second and third connector segments. This example medical device includes a leaflet attached to the support frame along an attachment pathway extending along the first and second connector struts and along a portion of the first connector segment and a portion of the second connector segment, the leaflet having an inner surface that defines a domed radius equal to or less than the expanded configuration radius when the support frame is in the expanded configuration. The domed radius can be any suitable domed radius, including a domed radius that is between about $\frac{1}{8}^{th}$ the expanded configuration radius and the expanded configuration radius, a domed radius that is between about $\frac{1}{4}^{th}$ the expanded configuration radius and about $\frac{3}{4}^{th}$ the expanded configuration radius, and a domed radius that is about $\frac{1}{4}^{th}$ the expanded configuration radius.

Another example medical device is similar to the example medical device described above, but also includes a second leaflet attached to the support frame along a second attachment pathway extending along the third and fourth connector struts and along a portion of the first connector segment and a portion of the second connector segment. Similar to the first leaflet, the second leaflet can have a domed radius equal to or less than the expanded configuration radius when the support frame is in the expanded configuration. For the second leaflet, the domed radius can be any suitable domed radius, including a domed radius that is between about $\frac{1}{8}^{th}$ the expanded configuration radius and the expanded configuration radius, a domed radius that is between about $\frac{1}{4}^{th}$ the expanded configuration radius and about $\frac{3}{4}^{th}$ the expanded configuration radius, and a domed radius that is about $\frac{1}{4}^{th}$ the expanded configuration radius.

In another example medical device having first and second leaflets, as briefly described above, the first and second leaflets have domed radii that are substantially equal. In another example medical device having first and second leaflets, as briefly summarized above, the first and second leaflets have domed radii that are equal.

Additional understanding of the inventive support frames and medical devices can be obtained with review of the detailed description, below, and the appended drawings.

DETAILED DESCRIPTION OF ILLUSTRATED EXAMPLE EMBODIMENTS

The following detailed description and the appended drawings describe and illustrate various example support frames and medical devices that are embodiments of the invention. The description and drawings are exemplary in nature and are provided to enable one skilled in the art to make and use one or more support frames or medical devices as an embodiment of the invention. The description and drawings are not intended to limit the scope of the claims in any manner.

Inventive intraluminal support frames and medical devices are described. The support frames are useful in the making of intraluminal medical devices, including the medical devices described herein. The support frames may also be useful as medical devices themselves, such as intraluminal stents. The medical devices can be used in any suitable intraluminal environment and to achieve any desired treatment effect in an animal, including human and non-human animals. For example, some of the example medical devices are useful for regulating fluid flow through a body vessel of a patient. As such, the medical devices can be used as valve devices. The medical devices also may be useful for other intraluminal purposes.

Support Frames

Figure 1:
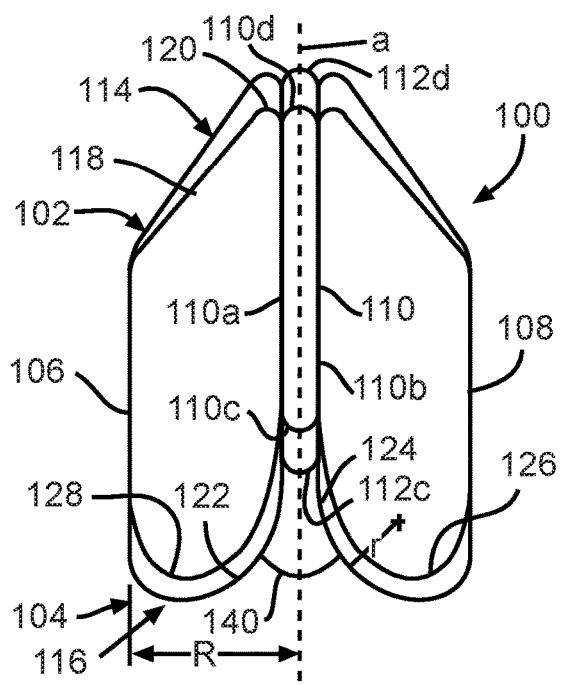
FIG. 1 is a perspective view of a first example support frame.
Figure 2:
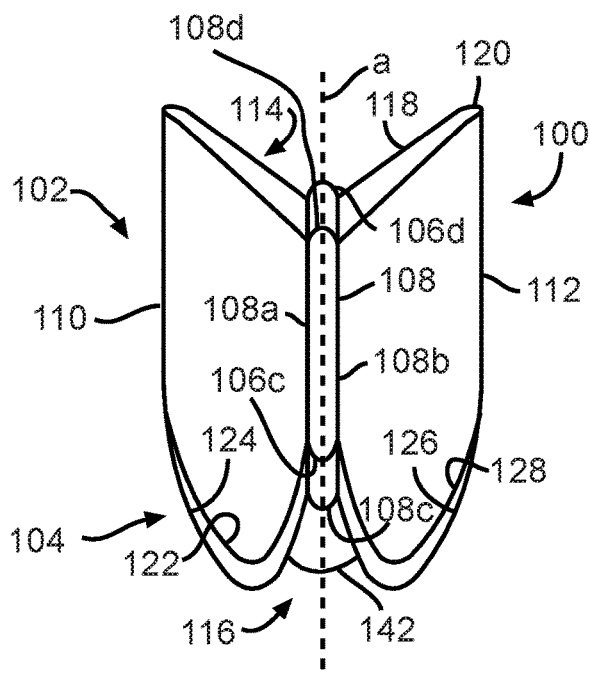
FIG. 2 another perspective view of the first example support frame, rotated ninety degrees from the view illustrated in FIG. 1.

FIGS. 1 and 2 illustrate a first example support frame 100.

The support frame 100 is an expandable support frame comprising proximal 102 and distal 104 portions connected by various connector segments 106, 108, 110, 112. The proximal portion 102 defines a first serpentine path 114 that extends around the circumference of the support frame 100. The distal portion 104 defines a second serpentine path 116 that also extends around the circumference of the support frame 100. The first serpentine path 114 includes pairs of straight strut portions 118 and bends 120, each of which is disposed between and connected to a circumferentially adjacent pair of the connector segments 106, 108, 110, 112. The second serpentine path 116 includes curvilinear struts 122, 124, 126, 128. Similar to the first serpentine path 114, each of the curvilinear struts 122, 124, 126, 128 is disposed between and connected to a circumferentially adjacent pair of the connector segments 106, 108, 110, 112. Thus, each serpentine path 114, 116 is joined to connector segments 106, 108, 110, 112.

In the illustrated embodiment, each of the connector segments 106, 108, 110, 112 includes first and second straight struts, designated by the corresponding reference number along with a or b, e.g., 110a, 110b, that are disposed parallel to each other. For each of the connector segments 106, 108, 110, 112, the straight struts are connected to each other by to curvilinear struts, designated by the corresponding reference number along with c or d, e.g., 110c, 110d. This arrangement of struts in the connector segments 106, 108, 110, 112 is considered advantageous at least because it provides a degree of structural redundancy and gives a secondary attachment point for associated materials and/or components in medical devices that include the support frame 100. In the illustrated embodiment, each of connector segments 106, 108, 110, 112 is disposed substantially on the circumferential plane of the support frame 100. It is noted, though, that one or more of the connector segments in a support frame according to a particular embodiment can be disposed entirely or partially outside of the circumferential plane of the support frame 100. For example, one or more connector segments may include a bend or curve that projects outwardly with respect to a longitudinal axis of the support frame. Connector segments with these structural features may be advantageous when additional surface area for contact with a wall of a body vessel and/or formation of an artificial sinus is desired, for example.

The support frame 100 illustrated in FIGS. 1 and 2 has four connector segments 106, 108, 110, 112. Pairs of these connector segments are disposed substantially opposite one another with respect to a longitudinal axis a of the support frame 100. Thus, connector segments 106 and 108 are disposed substantially opposite each other with respect to longitudinal axis a, and connector segments 110 and 112 are disposed substantially opposite each other with respect to longitudinal axis a. As a result, connector segments 106, 108, 110, 112 are distributed on the circumference of the support frame 100 such that each connector segment 106, 108, 110, 112 is positioned approximately equidistantly from two other connector segments 106, 108, 110, 112 along the circumference. It is noted, though, that, in all embodiments that include more than one connector segment, the connector segments can be distributed on the circumference of the support frame in any suitable manner. The illustrated distributions are merely examples of suitable distributions.

While the support frame 100 illustrated in FIGS. 1 and 2 includes four connector segments 106, 108, 110, 112, a support frame according to a particular embodiment can include any suitable number of connector segments. A skilled artisan will be able to determine an appropriate number of connector segments for a particular support frame based on various considerations, including the nature and size of the body vessel into which the support frame, or a medical device containing the support frame, is intended to be implanted and the nature of any materials and/or additional components that will be attached to the support frame in the fabrication of a medical device. When additional rigidity is desired, a greater number of connector segments can be included. When less is desired, one, two or three connector segments can be included. Furthermore, additional or fewer connector segments can be included to accommodate other materials and/or elements of a medical device in which the support frame is used. For example, the use of one, two or three connector segments may be advantageous in valve devices in which contact between a valve leaflet and a vessel wall is desirable.

In the illustrated embodiment, each of the curvilinear struts 122, 124, 126, 128 extends between and joins two of the connector segments 106, 108, 110, 112. For example, as best illustrated in FIG. 1, curvilinear strut 122 extends between and joins connector segments 106 and 110. Specifically, curvilinear strut 122 is connected to one curvilinear strut 110d of connector segment 110 and one curvilinear strut 106d of connector segment 106. Similarly, curvilinear strut 124 extends between and joins connector segments 108 and 110. Specifically, curvilinear strut 124 is connected to one curvilinear strut 110d of connector segment 110 and one curvilinear strut 108d of connector segment 108. As best illustrated in FIG. 2, curvilinear strut 126 extends between and joins connector segments 108 and 112. Thus, curvilinear strut 126 is connected to one curvilinear strut 118d of connector segment 108 and one curvilinear strut 112d of connector segment 112. While not visible in the FIGS., curvilinear strut 128 extends between and joins connector segments 112 and 106.

Inclusion of the curvilinear struts at only the distal end 104 of the support frame 100 provides directionality to the structure of the support frame 100, which is considered advantageous at least because it facilitates fabrication of medical devices that include the support frame 100. It is noted, though, that one or more curvilinear struts can be included on the proximal end, or at any other desirable location, of a support frame according to a particular embodiment.

Each curvilinear strut 122, 124, 126, 128 can have any suitable curvilinear configuration. A skilled artisan will be able to determine an appropriate configuration for a support frame according to a particular embodiment based on various considerations, including the nature of the body vessel within which the support frame is intended to be used, and the nature, size and configuration of any materials and/or additional elements that are attached to the support frame in the fabrication of a medical device that includes the support frame. Examples of suitable curvilinear configurations include curvilinear forms that define arcs, circular arcs, great arcs, s-curves, and others. Furthermore, in any particular embodiment, each curvilinear strut, if multiple curvilinear struts are included, can have the same or different curvilinear configuration as another of the curvilinear struts in the support frame. In the illustrated example embodiment, each of the curvilinear struts has the same curvilinear configuration. While considered advantageous for this illustrated example, this is merely an example of a suitable configuration and arrangement.

The inventors have determined that curvilinear struts that define circular arcs are particularly advantageous for inclusion in the support frames described herein. For example, each of the curvilinear struts 122, 124, 126, 128 in the embodiment illustrated in FIGS. 1 through 2 defines a circular arc.

For a curvilinear strut that defines an arc that is a circular arc or great arc, the arc can comprise a segment of the circumference of any suitable circle. As a result, the arc can have any suitable radius of curvature. A skilled artisan will be able to select an appropriate radius of curvature for such an arc for a support frame according to a particular embodiment based on various considerations, such as the nature and size of the body vessel within which the support frame is to be implanted, the number of curvilinear struts included in the support frame, and the nature, size and/or configuration of any additional material or elements included in a medical device within which the support frame is used.

The inventors have determined that a radius of curvature that is based on the radius of the circumference of the support frame in its expanded configuration provides desirable structural properties. For these structural measurements, the circumference of the support frame is a circumference of a transverse cross-section of the support frame with respect to the longitudinal axis of the support frame. The radius can be measured to either an inner or an outer circumferential surface, or a hypothetical circumferential surface by extension of an actual surface, of the support frame. For example, inclusion of one or more curvilinear struts that define an arc having a radius of curvature that is between about $1/16^{th}$ the radius of the circumference of the support frame in its expanded configuration and about 1× the radius of the circumference of the support frame in its expanded configuration is suitable. Additional examples of suitable radii of curvature for curvilinear struts include radii of curvature between about $1/8^{th}$ the radius of the circumference of the support frame in its expanded configuration and about 1× the radius of the circumference of the support frame in its expanded configuration is suitable, radii of curvature between about $\frac{1}{4}^{th}$ and about $\frac{3}{4}^{th}$ the radius of the circumference of the support frame in its expanded configuration, and a radius that is about $\frac{1}{2}$ the radius of the circumference of the support frame in its expanded configuration.

In the embodiment illustrated in FIGS. 1 and 2, the support frame 100 includes four curvilinear struts 122, 124, 126, 128, each of which defines an arc having a radius of curvature r that is about $\frac{1}{2}$ the radius R of the circumference of the support frame in its expanded configuration. The inventors have determined that this configuration and number of curvilinear struts 122, 124, 126, 128 is advantageous for inclusion on support frames according to particular embodiments at least because of the beneficial structural properties provided by the arrangement. Furthermore, as described in more detail below, the inventors have determined that this configuration and number of curvilinear struts 122, 124, 126, 128 is advantageous for inclusion in medical devices according to particular embodiments at least because of the attachment pathways defined by the curvilinear struts 122, 124, 126, 128.

In the illustrated embodiment, support frame 100 includes first 140 and second 142 support struts, each of which extends between and is connected to two of the curvilinear struts 122, 124, 126, 128. While considered optional, the inclusion of support struts 140, 142 may provide desirable structural properties for support frames and/or medical devices according to particular embodiments. If included, the support struts can have any suitable size and configuration. For example, the support struts can comprise straight struts or curvilinear struts. As illustrated in FIGS. 1 and 2, the support struts 140, 142 can comprise parabolic-shaped struts. Also, if included, the support struts can extend from the respective curvilinear struts at any suitable location on each of the curvilinear struts joined by the support strut. For example, as best illustrated in FIG. 1, support strut 140 extends from a point proximal to the curve defined by each of the joined curvilinear struts 122, 124. The inventors have determined that this positioning is advantageous at least because it provides desirable structural properties while not significantly interfering with the attachment pathway defined by the support frame 100 when the support frame 100 is used within a medical device and an additional material and/or additional element is attached to the curvilinear struts 122, 124 along the attachment pathway, as described below.

In all embodiments, the support frame advantageously comprises an expandable support frame having radially compressed and radially expanded configurations. Such a support frame can be implanted at a point of treatment within a body vessel by minimally invasive techniques, such as delivery and deployment with a catheter sized and conFIG.d for navigation within the body vessel. It is noted, though, that support frames and medical devices according to embodiments of the invention, regardless of the type and/or nature of the support frame, can be implanted by other techniques, including surgical techniques.

In all embodiments, the support frame can provide a stenting function, i.e., exert a radially outward force on the interior wall of a vessel in which the support frame, or medical device including the support frame, is implanted. By including a support frame that exerts such a force, a medical device according to the invention can provide multiple functions, such as a stenting and a valving function, at a point of treatment within a body vessel, which may be desirable in certain situations, such as when a degree of vessel stenosis, occlusion, and/or weakening is present.

Support frames according to particular embodiments can include additional structural elements, such as additional struts and bends. The inclusion of additional struts and/or bends may be desirable, for example, in support frames and medical devices intended for implantation at locations in the body where lower radial force on the tissue is desired. For these embodiments, the inclusion of additional struts and/or bends can distribute the radial force of the support frame across more structural elements, thereby reducing the radial force exerted by a particular portion of the support frame against tissue at a point of treatment. A support frame according to an embodiment can include conventional structural features that facilitate anchoring of the support frame at a point of treatment within a body vessel, such as barbs and/or microbarbs, and structural features, such as radiopaque markers, that facilitate visualization of the support frame in conventional or other medical visualization techniques, such as radiography, fluoroscopy, and other techniques. Furthermore, a support frame according to an embodiment can include structural features, such as eyelets, barbs, fillets and other suitable structures, that provide attachment points for grafts and other materials.

In all embodiments, the support frame can be self-expandable or can require an input of force to affect expansion, such as a balloon expandable support frame. Each type of support frame has advantages and for any given application, one type may be more desirable than other types based on a variety of considerations. For example, in the peripheral vasculature, vessels are generally more compliant and typically experience dramatic changes in their cross-sectional shape during routine activity. Support frames and medical devices for implantation in the peripheral vasculature should retain a degree of flexibility to accommodate these changes of the vasculature. Accordingly, support frames and medical devices according to the invention intended for implantation in the peripheral vasculature, such as valve devices, advantageously include a self-expandable support frame.

In all embodiments, the support frames can be made from any suitable material and a skilled artisan will be able to select an appropriate material for use in a support frame according to a particular embodiment based on various considerations, including any desired flexibility and visualization characteristics. The material selected for a support frame according to a particular embodiment need only be biocompatible or be able to be made biocompatible. Examples of suitable materials include, without limitation, stainless steel, nickel titanium (NiTi) alloys, e.g., Nitinol, other shape memory and/or superelastic materials, molybdenum alloys, tantalum alloys, titanium alloys, precious metal alloys, nickel chromium alloys, cobalt chromium alloys, nickel cobalt chromium alloys, nickel cobalt chromium molybdenum alloys, nickel titanium chromium alloys, linear elastic Nitinol wires, polymeric materials, and composite materials. Also, absorbable and bioremodellable materials can be used. As used herein, the term "absorbable" refers to the ability of a material to degrade and to be absorbed into a tissue and/or body fluid upon contact with the tissue and/or body fluid. A number of absorbable materials are known in the art, and any suitable absorbable material can be used. Examples of suitable types of absorbable materials include absorbable homopolymers, copolymers, or blends of absorbable polymers. Specific examples of suitable absorbable materials include poly-alpha hydroxy acids such as polylactic acid, polylactide, polyglycolic acid (PGA), or polyglycolide; trimethlyene carbonate; polycaprolactone; poly-beta hydroxy acids such as polyhydroxybutyrate or polyhydroxyvalerate; or other polymers such as polyphosphazines, polyorganophosphazines, polyanhydrides, polyesteramides, polyorthoesters, polyethylene oxide, polyester-ethers (e.g., polydioxanone) or polyamino acids (e.g., poly-L-glutamic acid or poly-L-lysine). There are also a number of naturally derived absorbable polymers that may be suitable, including modified polysaccharides, such as cellulose, chitin, and dextran, and modified proteins, such as fibrin and casein.

Stainless steel and nitinol are currently considered desirable materials for use in the support frame due at least to their biocompatibility, shapeability, and well-characterized nature. Also, cold drawn cobalt chromium alloys, such as ASTM F562 and ASTM F1058 (commercial examples of which include MP35N™ and Elgiloy™, both of which are available from Fort Wayne Metals, Fort Wayne, Ind.; MP35N is a registered trademark of SPS Technologies, Inc. Jenkintown, Pa., USA); Elgiloy is a registered trademark of Combined Metals of Chicago LLC (Elk Grove Village, Ill., USA)), are currently considered advantageous materials for the support frames at least because they are non-magnetic materials that provide beneficial magnetic resonance imaging (MRI) compatibility and avoid MRI artifacts typically associated with some other materials, such as stainless steel.

The support frames can be fabricated in any suitable manner and by any suitable technique. Skilled artisans will be able to select an appropriate manner and/or technique for fabricating a support frame according to a particular embodiment based on various considerations, including the nature of the material from which the support frame is being fabricated. Examples of suitable techniques include forming the support frame from wire, such as by wrapping a suitable wire around a suitable mandrel, by cutting the support frame from a tubular section of an appropriate material, such as by laser-cutting the support frame from a metal tubular member, and by forming the desired structure of the support frame in sheet form, such as by vapor deposition or other suitable technique, configuring the sheet into tubular form, such as by rolling or other suitable technique, and fixing the support frame in tubular form, such as by laser-welding or other suitable technique.

Figure 3:
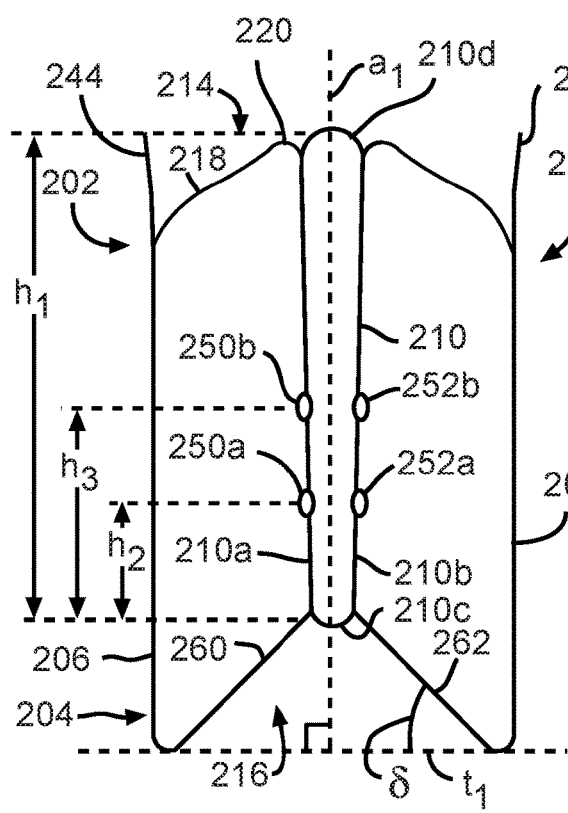
FIG. 3 is a side view of a second example support frame.
Figure 4:
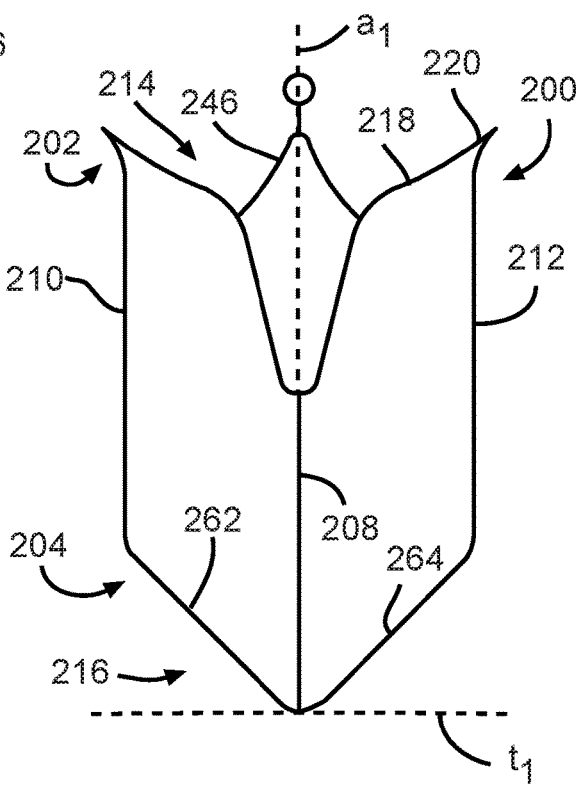
FIG. 4 is another side view of the second example support frame, rotated ninety degrees from the view illustrated in FIG. 3.
Figure 5:
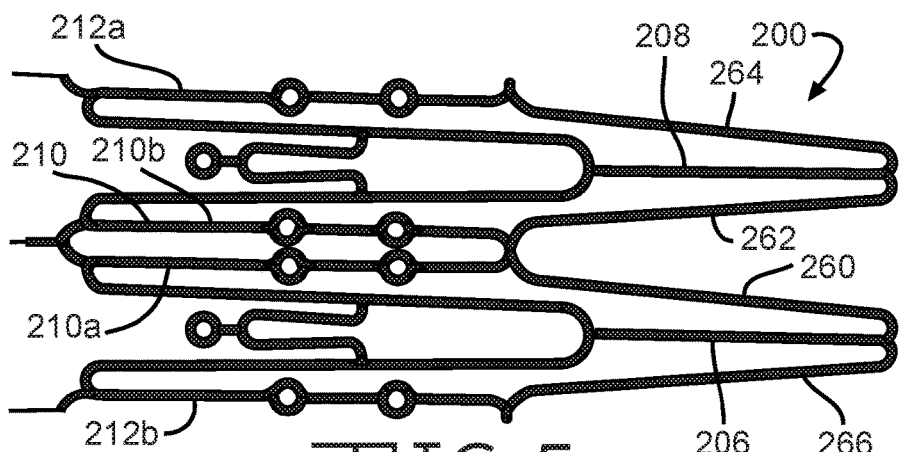
FIG. 5 is a flat plan view of the support frame illustrated in FIGS. 3 and 4.

FIGS. 3 through 5 illustrate a second exemplary support frame 200.

The support frame 200 of this embodiment is similar to support frame 100 illustrated in FIGS. 1 and 2 and described above, except as detailed below. Thus, support frame 200 is an expandable support frame comprising proximal 202 and distal 204 portions connected by various connector segments 206, 208, 210, 212. The proximal portion 202 defines a first serpentine path 214 that extends around the circumference of the support frame 200. The distal portion 204 defines a second serpentine path 216 that also extends around the circumference of the support frame 200. The first serpentine path 214 includes straight strut portions 218 and bends 220. Each serpentine path 214, 216 is joined to connector segments 206, 208, 210, 212.

Similar to the first exemplary embodiment, connector segments 206 and 208 are disposed substantially opposite each other with respect to longitudinal axis $a_1$, and connector segments 210 and 212 are disposed substantially opposite each other with respect to longitudinal axis $a_1$. The support frame 200 includes only two connector segments 210, 212 that each include first and second struts, designated by the corresponding reference number along with a or b, e.g., 210a, 210b. Remaining connector segments 206, 208 each include only a single strut. This configuration is considered advantageous for support frames and medical devices in which a reduction in the overall amount of surface area of the support frame is desirable.

Also, the first 210a and second 210b struts of the first connector segment 210 are disposed at a slight angle with respect to each other and longitudinal axis $a_1$, placing the struts 210a, 210b in a skewed arrangement with respect to each other. A parallel or substantially parallel arrangement of the struts that comprise a particular connector segment is considered advantageous, but a skewed arrangement, such as the arrangement illustrated in FIG. 3, can be used if desired. In this embodiment, the first strut 210a defines first 250a and second 250b eyelets. Similarly, the second strut 212b defines first 252a and second 252b eyelets. Each of the eyelets 250a, 250b, 252a, 252b is a ring-shaped structure defining an opening. As best illustrated in FIG. 3, the first eyelets 250a, 252a are disposed on the struts 210a, 210b such that the center of each eyelet 250a, 252a is positioned on a transverse axis of the support frame 200 that intersects the connector segment 210 at a point that is about ¼$^{th}$ of the height $h_1$ of the connector segment 210. The second eyelets 250b, 252b are disposed on the struts 210a, 210b such that the center of each eyelet 250b, 252b is positioned on a transverse axis of the support frame 200 that intersects the connector segment 210 at a point that is about ½ of the height $h_1$ of the connector segment 210. The inclusion of the eyelets 250a, 250b, 252a, 252b at these positions is considered advantageous at least because they provide attachment points at these positions for materials or additional elements included in medical devices that include the support frame 200, which can provide beneficial performance characteristics. If included, the eyelets can provide other and/or additional functional properties, also. For example, one or more eyelets can provide a structure for engagement by a suitable loading tool for placing a support frame or medical device within a delivery apparatus, such as a catheter. One or more eyelets can also be included to provide a structure for engagement by a suitable tool for withdrawing a support frame or medical device from a storage chamber, such as a hydration container within which a medical device is stored.

While the example support frame 200 includes four eyelets 250a, 250b, 252a, 252b, any suitable number of eyelets can be included in a support frame according to a particular embodiment. Furthermore, the each of the eyelets included in a support frame according to a particular embodiment can be placed at any suitable position on the connector segments for that support frame. Furthermore, the eyelet or eyelet on one straight strut in a connector segment can be positioned at the same or different position, relative to the height of the respective connector segment, as the eyelet or eyelets on another straight strut in a connector segment. A skilled artisan will be able to select an appropriate number of eyelets, an appropriate position for the eyelet or eyelets on the struts of a connector segment, and the relative distribution of the eyelet or eyelets on the straight struts of a connector segment in a support frame according to a particular embodiment based on various considerations, including any desired attachment points for an additional element, such as a graft or leaflet, that will be attached to the support frame, such as in the making of a medical device.

Also in this embodiment, the support frame 200 includes centering struts 244, 246, each of which extends in a proximal and radially outward direction from one of the straight strut portions 218 of the first serpentine path 214. The inventors have determined that the inclusion of centering struts 244, 246 provides beneficial deployment and positioning properties. For example, upon deployment in a body vessel, centering struts 244, 246 provide additional contact with the wall of the body vessel at the proximal portion 202 of the support frame 200, which can prevent or minimize tilting of the support frame 200 with respect to the longitudinal axes of the support frame 200 and the body vessel. If included, the centering struts can have any suitable size and configuration. For example, the centering struts can comprise straight struts, angled struts, a combination of straight struts and bends, as in the illustrated embodiment, or additional curvilinear struts. These struts, if included, can also provide a desirable location for placement of visualization makers, either as a structure fully or partially formed by these struts or as a structure attached to these struts.

In this embodiment, a series of connector struts 260, 262, 264, 266 extend between and join pairs of the connector segments 206, 208, 210, 212. Each of the connector struts 260, 262, 264, 266 extends between one of the connector segments 210, 212 that includes two struts, such as struts 210a and 210b, and one of the connector segments that includes only a single strut, such as connector segment 208. Thus, for example, connector strut 260 extends between and joins connector segments 210 and 206. Similarly, connector strut 262 extends between and joins connector segments 210 and 208.

Each of the connector struts 260, 262, 264, 266 lies on a plane that is disposed at an angle γ to a plane $t_1$ that orthogonally transects the longitudinal axis $a_1$ and includes the terminal structures of the distal portion 204 of the support frame 200. Each connector strut 260, 262, 264, 266 can lie on a plane disposed at any suitable angle. A skilled artisan will be able to determine an appropriate angle for each connector strut in a support frame according to a particular embodiment based on various considerations, including the nature of the body vessel within which the support frame is intended to be used, and the nature, size and configuration of any materials and/or additional elements that are attached to the support frame in the fabrication of a medical device that includes the support frame. Examples of suitable angles include angles between about 30° and about 50°, angles between about 30° and about 40°, and an angle that is about 35°.

While each of the connector struts 260, 262, 264, 266 in the illustrated embodiment is disposed at the same or substantially the same angle γ when the support frame is in its expanded configuration, different angles can be used for some or all of the connector struts. While considered advantageous, the illustrated configuration is merely an example of a suitable configuration.

Figures 6, 7:
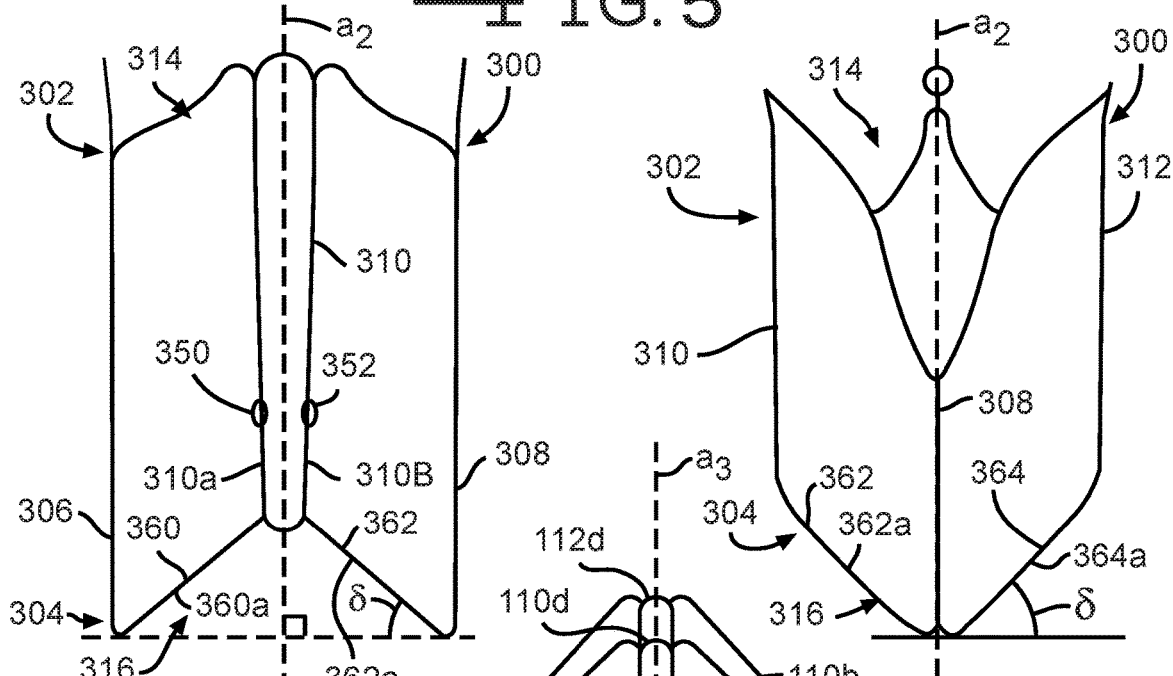
FIG. 6 is a side view of a third example support frame.
FIG. 7 is another side view of the third example support frame, rotated ninety degrees from the view illustrated in FIG. 6.

FIGS. 6 and 7 illustrate a third example support frame 300.

The support frame 300 of this embodiment is similar to support frame 200 illustrated in FIGS. 3 through 5 and described above, except as detailed below. Thus, support frame 300 is an expandable support frame comprising proximal 302 and distal 304 portions connected by various connector segments 306, 308, 310, 312. The proximal portion 302 defines a first serpentine path 314 that extends around the circumference of the support frame 300. The distal portion 304 defines a second serpentine path 316 that also extends around the circumference of the support frame 300. The first serpentine path 314 includes straight strut portions 318 and bends 320. Each serpentine path 314, 316 is joined to connector segments 306, 308, 310, 312.

Connector segments 306 and 308 are disposed substantially opposite each other with respect to longitudinal axis $a_1$, and connector segments 310 and 312 are disposed substantially opposite each other with respect to longitudinal axis $a_1$. Similar to the embodiment illustrated in FIGS. 3 through 5 and illustrated above, the support frame 300 includes only two connector segments 310, 312 that each include first and second struts, designated by the corresponding reference number along with a or b, e.g., 310a, 310b. Remaining connector segments 306, 308 each include only a single strut.

In this embodiment, the pair of struts that define each of connector segments 310 and 312 are disposed substantially parallel to each other. Also, each of the struts in the pair of struts that define each of connector segments 310 and 312 defines a single eyelet. Thus, as best illustrated in FIG. 6, the first strut 310a of connector segment 310 defines eyelet 350 and the second strut 310b defines eyelet 352. Each of the eyelets 350, 352 is a ring-shaped structure defining an opening. In this embodiment, each of the eyelets 350, 352 is disposed on the respective strut 310a, 310b such that the center of each eyelet 350, 352 is positioned on a transverse axis of the support frame 300 that orthogonally intersects the connector segment 310 at a point that is about $¼^{th}$ of the height $h_1$ of the connector segment 310. It is noted that, while the illustrated eyelets 350, 352 pass through the entire thickness of the respective struts 310a, 310b from one surface to an opposing surface, any other suitable structure can be used, such as passageways that pass through a partial thickness of the respective strut and/or blind openings.

In this embodiment, a series of connector struts 360, 362, 364, 366 extend between and join pairs of the connector segments 306, 308, 310, 312. Each of the connector struts 360, 362, 364, 366 extends between one of the connector segments 310, 312 that includes two struts, such as struts 310a and 310b, and one of the connector segments that includes only a single strut, such as connector segment 308. Thus, for example, connector strut 360 extends between and joins connector segments 310 and 306. Similarly, connector strut 362 extends between and joins connector segments 310 and 308.

In this embodiment, each of the connector struts 360, 362, 364, 366 is a curvilinear strut that includes a straight portion, designated by the corresponding reference number along with a. The straight portion 360a, 362a, 364a, 366a of each of the connector struts 360, 362, 364, 366 lies on a plane that is disposed at an angle γ to a plane that orthogonally transects the longitudinal axis $a_1$ and includes the terminal structures of the distal portion 304 of the support frame 300. Each connector strut 360, 362, 364, 366 can lie on a plane disposed with its respective straight portion 360a, 362a, 364a, 366a at any suitable angle. A skilled artisan will be able to determine an appropriate angle for each connector strut in a support frame according to a particular embodiment based on various considerations, including the nature of the body vessel within which the support frame is intended to be used, and the nature, size and configuration of any materials and/or additional elements that are attached to the support frame in the fabrication of a medical device that includes the support frame. Examples of suitable angles include angles between about 30° and about 50°, angles between about 30° and about 40°, and an angle that is about 35°.

While each of the connector struts 360, 362, 364, 366 in the illustrated embodiment is disposed with the respective straight portion 360a, 362a, 364a, 366a at the same or substantially the same angle γ when the support frame is in its expanded configuration, different angles can be used for some or all of the connector struts. While considered advantageous, the illustrated configuration is merely an example of a suitable configuration.

Figure 6A:
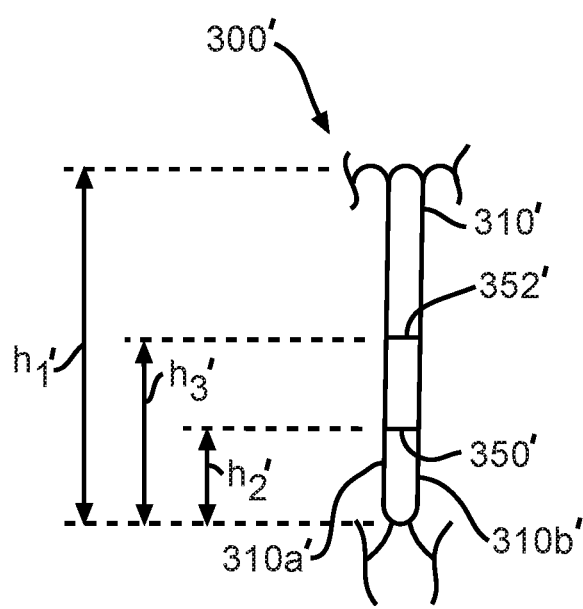
FIG. 6A is a partial side view of an alternate support frame.
Figure 6B:
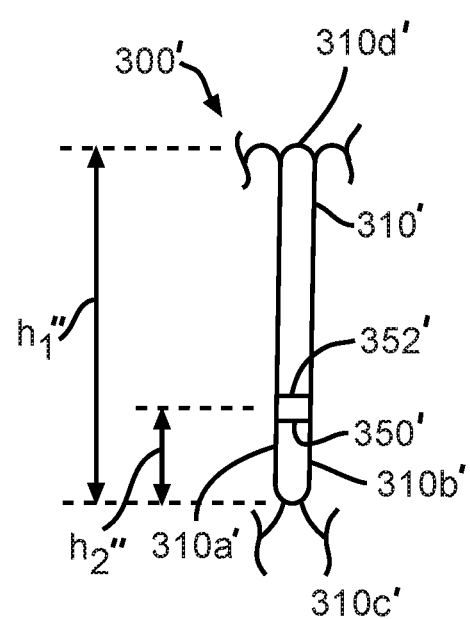
FIG. 6B is a partial side view of another alternate support frame.

Each of FIGS. 6A and 6B illustrate a connector segment 310' of an alternative support frame. In each figure, the connector segment 310' includes alternative structure for the eyelets 350, 352 illustrated in FIG. 6. In these alternative embodiments, bars 350', 352' are included instead of the eyelets. The purpose of the bars 350', 352' is the same as the eyelets 350, 352 illustrated in FIG. 6, but the structure is different. Instead of defining an opening, each bar 350', 352' is a straight member or substantially straight member that extends between the pair of struts 310a', 310b' that define a connector segments 310'. If included in a support frame or medical device according to a particular embodiment, any suitable number of bars can be included and each of the included bars can be placed in any suitable position. In each of FIGS. 6A and 6B, two bars 350', 352' are included, but each figure illustrates a different relative positioning for the bars 350', 352'.

If included, the bars 350', 352' can be positioned in a similar manner as the eyelets 350, 352 in the support frame 300 illustrated in FIG. 6. Thus, as illustrated in FIGS. 6A and 6B, one bar 350' is disposed on the respective struts 310a', 310b' such that the lengthwise axis of the bar 350' is positioned on a transverse axis of the support frame 300' that orthogonally intersects the connector segment 310' at a point that is about $\frac{1}{4}^{th}$ of the height $h_1'$ of the connector segment 310'. This height is represented as $h_2'$ in FIGS. 6A and 6B.

Inclusion of additional bars is optional. If included, any additional bars can be positioned at any suitable location on the connector segment 310'. FIGS. 6A and 6B illustrate example positioning for a second bar 352'. In FIG. 6A, a second bar 352' is disposed on the respective struts 310a', 310b' such that the lengthwise axis of the bar 352' is positioned on a transverse axis of the support frame 300' that orthogonally intersects the connector segment 310' at a point that is about ½ of the height $h_1'$ of the connector segment 310'. This height is represented as $h_3'$ in FIG. 6A. In this arrangement, the second bar 352' is largely independent of the first bar 350' and provides a second, independent point of attachment for additional materials, such as a valve leaflet or graft material.

In FIG. 6B, a second bar 352' is disposed on the respective struts 310a', 310b' such that the bar is associated closely with the first bar 350'. In this embodiment, a hypothetical line extending between the pair of struts 310a', 310b' that define connector segment 310' and that is spaced equidistantly from each of the bars 350', 352' is positioned on a transverse axis of the support frame 300' that orthogonally intersects the connector segment 310' at a point that is about $\frac{1}{4}^{th}$ of the height $h_1'$ of the connector segment 310'. This height is represented as $h_2'$ in FIGS. 6A and 6B. In this arrangement, the second bar 352' is paired with the first bar 350' to cooperatively define an opening that provides a point of attachment for additional materials, such as a valve leaflet or graft material.

Medical Devices

Figure 8:
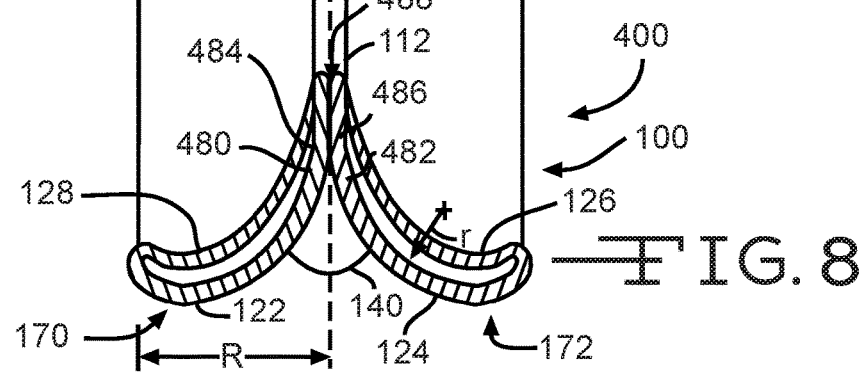
FIG. 8 is a perspective view of a first example medical device.

FIG. 8 illustrates a first exemplary medical device 400.

The medical device 400 is a valve device that includes the first example support frame 100 illustrated in FIGS. 1 and 2 and first 480 and second 482 leaflets. The first leaflet 480 is attached to the support frame 100 along a first attachment pathway 170 that extends along curvilinear struts 122, 128 and along a portion of connector segments 110, 112. Similarly, the second leaflet 482 is attached to the support frame 100 along a second attachment pathway 172 that extends along curvilinear struts 124, 126 and along a portion of connector segments 110, 112. Each leaflet 480, 482 has a free edge 484, 486 that is not attached to the support frame 100. The free edges 484, 486 cooperatively define valve orifice 488.

The medical device 400 is a valve device that is useful for regulating fluid flow through a body vessel. Each of the leaflets 480, 482 is movable between first and second positions. In the first position, the orifice 488 is open and allows fluid flow through the device 400 in a first direction. In the second position, the free edges 484, 486 of leaflets 480, 482 come together to close the orifice 488 and substantially prevent fluid flow through the device 400 in a second, opposite direction.

Each of the leaflets 480, 482 can have any suitable size, shape and/or configuration. A skilled artisan will be able to select leaflets having appropriate size, shape and configuration properties for a medical device according to a particular embodiment based on various considerations, including any desired performance characteristics of the medical device. The inventors have determined that leaflets that, when attached to a support frame and when the support frame is in an expanded configuration and the leaflets subjected to fluid pressure sufficient to effect closure of the valve orifice, define a domed radius of curvature, i.e., a portion of one surface of the leaflet lies on a portion of a spherical plane or substantially spherical plane, provide desirable performance characteristics for medical devices intended to be used as valve devices, such as prosthetic venous valve devices. In these embodiments, the portion of a spherical plane or substantially spherical plane can comprise a portion of the spherical plane of any suitable sphere. As a result, the portion of a spherical plane or substantially spherical plane can have any suitable radius of curvature. Also in these embodiments, the portion the surface of the leaflet that defines the domed radius can comprise any suitable portion of the leaflet surface, including a central portion that does not contact any struts or other structural members of the associated support frame, a base portion that is positioned at the bottom of a valve pocket formed in the valve device when the valve orifice is closed, or any other suitable portion of the leaflet surface. A skilled artisan will be able to select an appropriate portion of the leaflet surface and an appropriate radius of curvature for a medical device according to a particular embodiment based on various considerations, including the nature and size of the body vessel within which the medical device is to be implanted, and the nature of the material from which the leaflets are formed. Also, it is noted that the domed radii described herein are present in the respective leaflet at least when the leaflet is subjected to fluid pressure sufficient to close the associated valve orifice, such as when the medical device containing the leaflet is exposed to such fluid pressure in vivo or in suitable testing environments, such as in a vessel simulator or a simple fluid container.

The inventors have determined that leaflets defining a domed radius that is based on the radius of the circumference of the support frame in its expanded configuration provides desirable structural properties. For example, inclusion of one or more curvilinear leaflets that define a domed radius having a radius of curvature that is between about $\frac{1}{8}^{th}$ the radius of the circumference of the support frame in its expanded configuration and about 1× the radius of the circumference of the support frame in its expanded configuration is suitable. Additional examples of suitable radii of curvature include radii of curvature between about $\frac{1}{4}^{th}$ and about $\frac{3}{4}^{th}$ the radius of the circumference of the support frame in its expanded configuration, and a radius that is about ½ the radius of the circumference of the support frame in its expanded configuration.

The exemplary medical device 400 is illustrated with the support frame 100 in an expanded configuration and with the leaflets 480, 482 in the configuration they adopt when subjected to fluid pressure sufficient to effect closure of the valve orifice. As illustrated in the FIG., in this state, each of the leaflets 480, 482 defines a domed radius of curvature r that is about ½ the radius R of the circumference of the support frame 100 in its expanded configuration. The inventors have determined that this configuration of the leaflets 480, 482 is advantageous at least because of the beneficial performance characteristics provided by the arrangement.

It is noted that, while the medical device 400 is illustrated as including support frame 100, any suitable support frame that positions the leaflets 480, 482 in the desired configuration, i.e., with the domed radius, can be used. For example, leaflets can be attached to any of the support frame described and illustrated herein such that the desired configuration is achieved. A skilled artisan will be able to select an appropriate support frame for a medical device according to a particular embodiment based on various considerations, including the nature, size and configuration of the material forming the leaflets.

Figure 9:
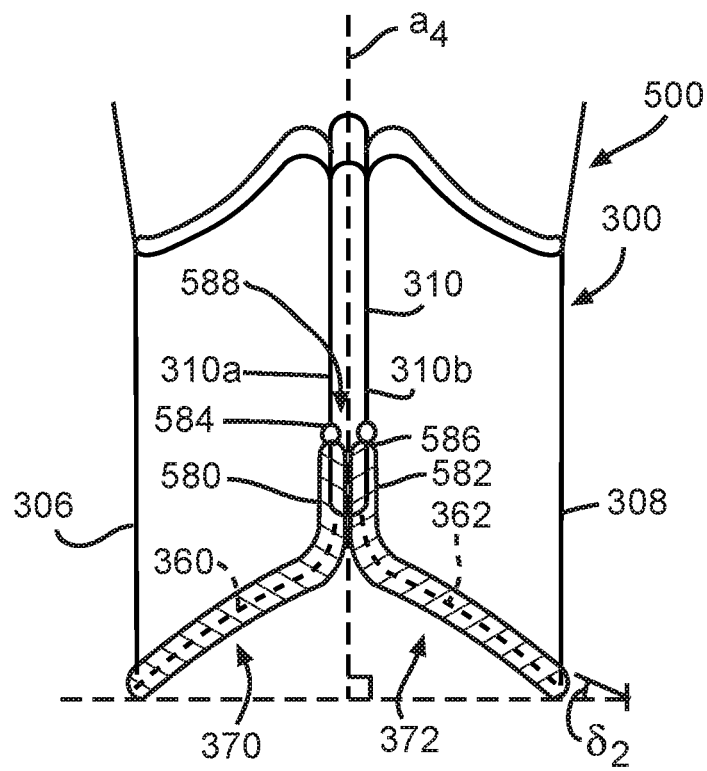
FIG. 9 is a side view of a second example medical device.
Figure 10:
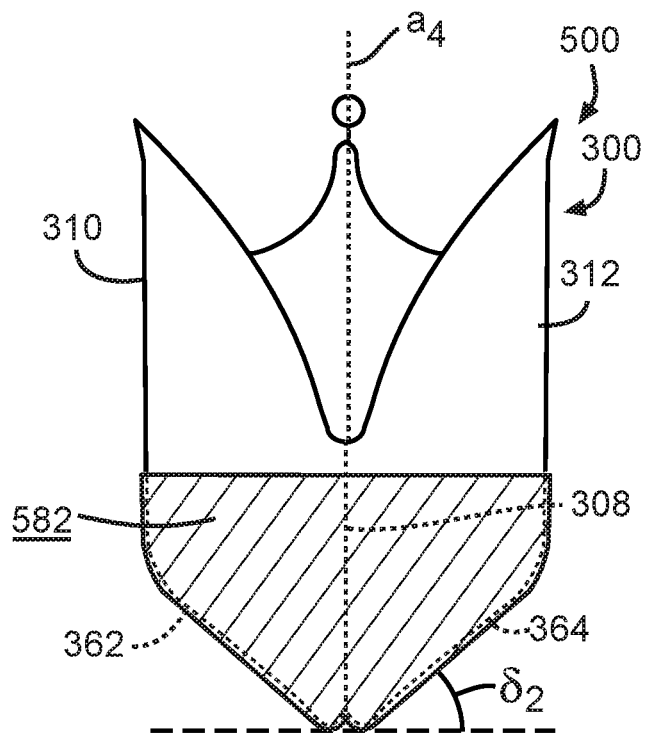
FIG. 10 is another side view of the second example medical device, rotated ninety degrees from the view illustrated in FIG. 9.

FIGS. 9 and 10 illustrate a second example medical device 500.

The medical device 500 is a valve device that includes the third exemplary support frame 300 illustrated in FIGS. 6 and 7 and first 580 and second 582 leaflets. The first leaflet 580 is attached to the support frame 300 along a first attachment pathway 370 that extends along connector struts 360, 366 and along a portion of connector segments 310, 312. Similarly, the second leaflet 582 is attached to the support frame 300 along a second attachment pathway 372 that extends along connector struts 362, 364 and along a portion of connector segments 310, 312. Each leaflet 580, 582 has a free edge 584, 586 that is not attached to the support frame 300. The free edges 584, 586 cooperatively define valve orifice 588.

The medical device 500 is a valve device that is useful for regulating fluid flow through a body vessel. Each of the leaflets 580, 582 is movable between first and second positions. In the first position, the orifice 588 is open and allows fluid flow through the device 500 in a first direction. In the second position, the free edges 584, 586 of leaflets 580, 582 come together to close the orifice 588 and substantially prevent fluid flow through the device 500 in a second, opposite direction.

In this embodiment, each attachment pathway 370, 372 extends along a portion of the axial length of connector segment 310 and along a portion of the axial length of connector segment 312. For each attachment pathway 370, 372 and each connector segment 310, 312, the portion of the axial length of the connector segment 310, 312 along which the attachment pathway extends can be any suitable portion of the axial length of the connector segment 310, 312, including the entire axial length of the connector segment 310, 312. For each attachment pathway and each connector segment in a medical device according to a particular embodiment, a skilled artisan will be able to select an appropriate portion of the axial length along which the attachment pathway extends based on various considerations, such as the nature, size and configuration of the leaflets or other material and/or additional elements included in the medical device.

The inventors have determined that a portion of the axial length of the connector segment along which the attachment pathway extends that is between about $1/16^{th}$ the full axial length of the connector segment and about the full axial length of the connector segment is suitable. Additional examples of suitable portions of the axial length of the connector segments along which the attachment pathways extend include portions of the axial length of the connector segments that are between about $1/8^{th}$ the full axial length of the connector segment and about $3/4^{th}$ the full axial length of the connector segment, and portions of the axial length of the connector segments that are between about $1/4^{th}$ the full axial length of the connector segment and about ½ the full axial length of the connector segment.

In the embodiment illustrated in FIGS. 9 and 10, each of the attachment pathways 370, 372 extends along a portion of each connector segment 310, 312 that is equal to about $1/4^{th}$ the full axial length of the respective connector segment 310, 312. In this embodiment, the connector segments 310, 312 have approximately equal axial lengths, so the portions of the axial lengths along which the attachment pathways 370, 372 extend are also approximately equal. The inventors have determined that this configuration of the attachment pathways 370, 372 is advantageous for inclusion in medical devices according to particular embodiments at least because it provides desirable performance characteristics.

In any particular embodiment, the attachment pathways, if included, can extend along the same or different portion of the axial length of each connector segment. For example, a medical device according to an embodiment can include a first attachment pathway that extends along approximately equal portions of the axial lengths of first and second connector segments and a second attachment pathway that extends along approximately equal portions of the axial lengths of the first and second connector segments that are different than the portions along which the first attachment pathway extends. Furthermore, a medical device according to an embodiment may include one or more attachment pathways that extends along a portion of the axial length of a first connector segment and along a portion of the axial length of a second connector segment that is less than, equal to, approximately equal to, or greater than the portion of the axial length of the first connector segment.

In the illustrated embodiment, the attachment pathways 370, 372 also extend along connector struts 360, 362, 364, 366 that extend between and join adjacent pairs of connector segments 306, 308, 310, 312. If included, any suitable connector struts can be used in a medical device according to a particular embodiment and a skilled artisan will be able to select appropriate connector struts based on various considerations, including the nature of the material from which the element(s) being attached to the support frame, such as leaflets, is formed. As illustrated in FIGS. 9 and 10, connector struts 360, 362, 364, 366 that each comprise a curvilinear strut that includes a straight portion, designated by the corresponding reference number along with a, are considered suitable. In the illustrated embodiment, the straight portion 360a, 362a, 364a, 366a of each of the connector struts 360, 362, 364, 366 lies on a plane that is disposed at an angle $\gamma_2$ to a plane that orthogonally transects the longitudinal axis a4 and includes the terminal structures of the distal portion 304 of the support frame 300. Each connector strut 360, 362, 364, 366 can be disposed with its respective straight portion 360a, 362a, 364a, 366a at any suitable angle. A skilled artisan will be able to determine an appropriate angle for each connector strut in a support frame according to a particular embodiment based on various considerations, including the nature of the body vessel within which the support frame is intended to be used, and the nature, size and configuration of any materials and/or additional elements that are attached to the support frame in the fabrication of a medical device that includes the support frame. Examples of suitable angles include angles between about 30° and about 50°, angles between about 30° and about 40°, and an angle that is about 35°.

Figure 11:
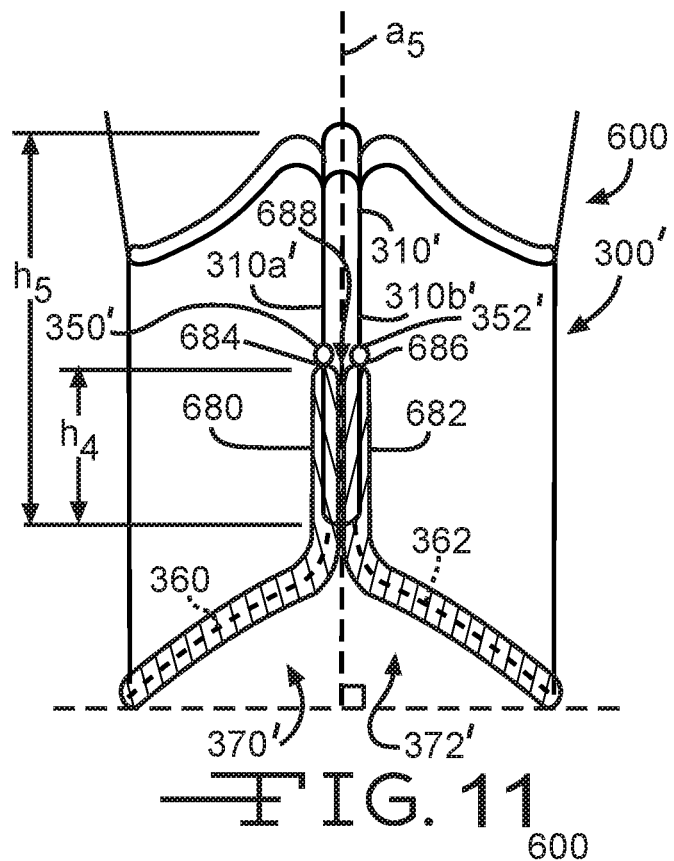
FIG. 11 is a side view of a third example medical device.
Figure 12:
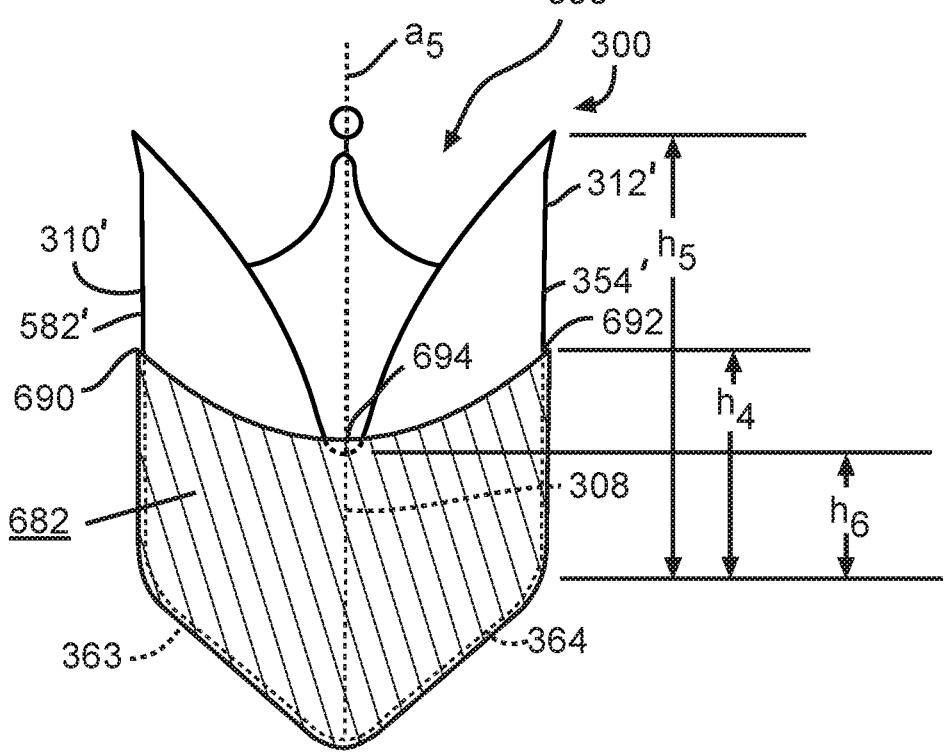
FIG. 12 is another side view of the third example medical device, rotated ninety degrees from the view illustrated in FIG. 11.

FIGS. 11 and 12 illustrate a third example medical device 600.

The medical device 600 is a valve device that includes a modified version of the third exemplary support frame 300' illustrated in FIGS. 6 and 7 and first 680 and second 682 leaflets. The medical device 600 is similar to the second exemplary medical device 500 described above and illustrated in FIGS. 9 and 10, except as detailed below. The first leaflet 680 is attached to the support frame 300' along a first attachment pathway 370' that extends along connector struts 360, 366 and along a portion of connector segments 310', 312'. Similarly, the second leaflet 682 is attached to the support frame 300' along a second attachment pathway 372' that extends along connector struts 362, 364 and along a portion of connector segments 310', 312'. Each leaflet 680, 682 has a free edge 684, 686 that is not attached to the support frame 300. The free edges 684, 686 cooperatively define valve orifice 688.

The medical device 600 is a valve device that is useful for regulating fluid flow through a body vessel. Each of the leaflets 680, 682 is movable between first and second positions. In the first position, the orifice 688 is open and allows fluid flow through the device 600 in a first direction. In the second position, the free edges 684, 686 of leaflets 680, 682 come together to close the orifice 688 and substantially prevent fluid flow through the device 600 in a second, opposite direction.

In this embodiment, support frame 300 includes eyelets 350', 352', 354', 356'. The first 310a' strut of the first connector segment 310' defines eyelet 350'. Similarly, the second strut 310b' of the first connector segment 310' defines eyelet 354'. Similarly, the first 312a' and second 312b' struts of the second connector segment each defines one of remaining eyelets 354', 356'. Each of the eyelets is a ring-shaped structure defining an opening. As best illustrated in FIG. 11, each of the 350', 352', 354', 356' is disposed on the respective strut 310a', 310b', 312a', 312b' of the respective connector segment 310', 312' such that the center of each eyelet 350', 352', 354', 356' is positioned on a transverse axis of the support frame 300' that intersects the connector segments 310', 312' at a point corresponding to a height $h_4$ that is about ½ of the height $h_5$ of the respective connector segment 310', 312'. The inclusion of the eyelets 350', 352', 354', 356' at these positions is considered advantageous at least because they provide attachment points at these positions for the leaflets 680, 682, which can provide beneficial performance characteristics.

In this embodiment, the free edge 684, 686 of each leaflet defines a curve. If leaflets having this structure are included, any suitable curve can be used and a skilled artisan will be able to select an appropriate curve or curves based on various considerations, including the nature of the material from which the leaflets are formed. As best illustrated in FIG. 12, a parabolic curve is considered suitable. Indeed, the inventors have determined that a parabolic curve that, when the respective leaflet 682 is attached to the support frame 300, extends inwardly from points 690, 692 on the respective attachment pathway 372 that correspond to a height $h_4$ is about ½ of the height $h_5$ of the respective connector segment 312' to an apex 694 that is at a point that corresponds to a height $h_6$ that is about ¼th of the height $h_5$ of the respective connector segment 312', is considered suitable.

If a leaflet having a free edge defining a curve is used, the curve can be formed prior to attaching the leaflet to the support frame, or can be formed following attachment of the leaflet to the support frame, such as by cutting the leaflet to create a free edge defining a desired curve.

In all embodiments, any suitable materials and/or additional elements can be attached to the support frame to form a medical device. A skilled artisan will be able to select an appropriate material for use with a support frame in a medical device according to a particular embodiment based on various considerations, including the intended use and desired function of the medical device. For valve devices, such as the valve device illustrated in FIGS. 9 and 10, each of the leaflets 580, 582 comprises a section of material, such as a sheet, that is attached to the support frame 300 along a respective attachment pathway 370, 372, as described above. The leaflets 580, 582 can be formed of any suitable material, and need only be biocompatible or be able to be made biocompatible. The material can advantageously be formed of a flexible material. Examples of suitable materials for use as leaflets in medical devices that comprise valve devices include natural materials, synthetic materials, and combinations of natural and synthetic materials. Examples of suitable natural materials include extracellular matrix (ECM) materials, such as small intestine submucosa (SIS), and other bioremodelable materials, such as bovine pericardium. Other examples of suitable ECM materials that can be used include stomach submucosa, liver basement membrane, urinary bladder submucosa, tissue mucosa, and dura mater. Other examples of suitable natural materials include renal capsule matrix, abdominal fascia, parenchyma, such as abdominal parenchyma, connective tissue, pulmonary or lung ligament, tissue laminates, and natural valve leaflets with or without adjacent vessel wall. Pleura is also considered a suitable natural material, including visceral pleura. Fixed tissues are also considered suitable, including fixed SIS, fixed pericardium, fixed pulmonary or lung ligament, and any other suitable fixed natural tissue. When fixed tissue is used, any suitable fixation technique and/or procedure can be used, including chemical fixatives, such as aldehydes, e.g., formaldehyde, gluteraldehyde, and formalin, and carbodiimides, such as ethyl dimethylaminopropyl carbodiimide, dicyclohexylcarbodiimide. Physical fixation techniques and/or procedures can also be used, including exposure to heat and/or radiation. Lyophilized preparations and chemically-dried preparations of these natural materials are also considered suitable. Examples of suitable synthetic materials include polymeric materials, such as expanded polytetrafluoroethylene, polyurethane, polyurethane urea, polycarbonate, and polyesters.

Any attached materials can have any suitable size, shape and configuration. For example, valve devices can include one, two or more leaflets that are sheet-like sections of material attached to a support frame according to an embodiment. Another example of a material that can be attached to a support frame according to an embodiment is a tubular structure that is attached around the outer circumference of the support frame. Indeed, a tubular structure and one, two or more leaflets can be attached to a support frame according to an embodiment to form a valve device having an outer sleeve.

In all embodiments including additional material and/or elements attached to the support frame, the additional material and/or elements can be attached to the support frame in any suitable manner and with any suitable structure and/or substance. For example, leaflets can be attached to a support frame in a valve device using sutures, tissue welding, adhesive(s), mechanical attachment(s), a combination of these approaches, and any other suitable structure and/or substance.

In all embodiments including an additional material and/or elements attached to the support frame, the additional material and/or elements can be attached to the support frame in any suitable orientation. A skilled artisan will be able to select a suitable orientation for a particular material or element attached to the support frame in a specific embodiment based on various considerations, including the physical properties of the material or element and any desired properties of the resulting medical device that may be impacted by the orientation of the material or element. For example, for valve devices that include one or more leaflets attached to the support frame, it may be desirable to attach the leaflet or leaflets in a particular orientation based on the ability of the leaflet to stretch in a particular direction. Anisotropic materials may be able to stretch to a greater degree along one axis than along another axis. The inventors have determined that, when attaching an anisotropic material to a support frame to form a medical device, it may be desirable to attach the material in an orientation in which the axis along which the material has a greater ability to stretch is aligned with the longitudinal axis of the support frame if it is desirable to have the leaflet of the medical device form a relatively deeper valve pocket when the medical device is subjected to sufficient fluid pressure to move the leaflet to a closed position. Conversely, the inventors have determined that it may be desirable to attach the material in an orientation in which the axis along which the material has a greater ability to stretch is aligned in a transverse orientation to the longitudinal axis of the support frame if it is desirable to have the leaflet of the medical device form a relatively larger valve orifice when the medical device is subjected to sufficient fluid pressure to move the leaflet to an open position.

For valve devices, the inventors have determined that attaching a leaflet to a support frame described herein while the leaflet is held in an open position can provide desirable performance characteristics to the resulting valve device. Specifically, the inventors have determined that attaching a leaflet to a support frame described herein while the leaflet is held in an open position on a mandrel such that a degree of slack is provided in a portion of the leaflet that will have a domed radius can provide desirable performance characteristics to the resulting valve device.

Furthermore, while the medical devices described and illustrated herein are valve devices, it is noted that other types of medical devices can be made in accordance with the disclosure. For example, a vessel occluder can include a support frame according to an embodiment along with leaflets that are sewn or otherwise attached to each other to permanently close an associated valve orifice or a graft material that lacks an orifice.

The support frames and medical devices can be implanted within a body vessel at a desired point of treatment using conventional minimally-invasive techniques, such as by delivery with an associated catheter, by surgical techniques, or by any other suitable technique for placing a support frame or medical device at a point of treatment within a body vessel.

The foregoing detailed description refers to example support frames and medical devices and includes the best mode for practicing the invention. The description and the appended drawings illustrating the described devices are intended only to provide examples and not to limit the scope of the claims in any manner.

What is claimed is:

1. A medical device for regulating fluid flow through a body vessel of a patient, comprising:
   an expandable support frame having a longitudinal axis, an outer circumference, and an unexpanded configuration, the support frame comprising:
      a first connector segment having an axial length and comprising substantially parallel first and second struts and a first connecting bar extending between and joining the first and second struts;
      a second connector segment having an axial length and disposed substantially opposite the first connector segment with respect to said longitudinal axis, the second connector segment comprising substantially parallel third and fourth struts and a second connecting bar extending between and joining the third and fourth struts;
      a third connector segment disposed circumferentially adjacent the first and second connector segments, the third connector segment being only a single strut;
   a fourth connector segment disposed substantially opposite the third connector segment with respect to said longitudinal axis;
      a proximal portion defining a first circumferential serpentine path joined to the first, second, third, and fourth connector segments; and
      a distal portion defining a second circumferential serpentine path joined to the first, second, third, and fourth connector segments and comprising a first connector strut extending between and joining the first and third connector segments, a second connector strut extending between and joining the second and third connector segments, a third connector strut extending between and joining the first and fourth connector segments, and a fourth connector strut extending between and joining the second and fourth connector segments, each of the first connector strut, the second connector strut, the third connector strut, and the fourth connector strut comprising a curvilinear strut that includes a straight portion;
   a first leaflet attached to the support frame along an attachment pathway extending along the first and second connector struts and only along a first portion of the first connector segment extending from the distal portion and toward the proximal portion and a first portion of the second connector segment extending from the distal portion and toward the proximal portion, the first leaflet having a first free edge and a first inner surface; and
   a second leaflet attached to the support frame along a second attachment pathway extending along the third and fourth connector struts and along a second portion of the first connector segment and a second portion of the second connector segment, the second leaflet having a second free edge and a second inner surface;
   wherein the first and second free edges cooperatively define a valve orifice;
   wherein the first portion of the first connector segment is between about $\frac{1}{8}^{th}$ and about $\frac{3}{4}^{th}$ the axial length of the first connector segment;
   wherein the first portion of the second connector segment is between about $\frac{1}{8}^{th}$ and about $\frac{3}{4}^{th}$ the axial length of the second connector segment; and wherein the single strut extends from the proximal portion to the first connector strut and the second connector strut.

2. The medical device of claim 1, wherein the first portion of the first connector segment is about $\frac{1}{4}^{th}$ the axial length of the first connector segment.

3. The medical device of claim 2, wherein the first portion of the second connector segment is about $\frac{1}{4}^{th}$ the axial length of the second connector segment.

4. The medical device of claim 3, wherein the first connecting bar is positioned on a first transverse axis of the support frame that orthogonally intersects the first connector segment at a point that is about $\frac{1}{4}^{th}$ the axial length of the first connector segment; and wherein the second connecting bar is positioned on a second transverse axis of the support frame that orthogonally intersects the second connector segment at a point that is about $\frac{1}{4}^{th}$ the axial length of the second connector segment.

5. The medical device of claim 1, further comprising a third connecting bar extending between the first and second struts.

6. The medical device of claim 1, wherein the support frame is free of additional struts between the first connector segment and the third connector segment.

7. The medical device of claim 6, wherein the support frame is free of additional struts between the second connector segment and the third connector segment.

8. The medical device of claim 7, wherein the support frame is free of additional struts between the first connector segment and the fourth connector segment.

9. The medical device of claim 8, wherein the support frame is free of additional struts between the second connector segment and the fourth connector segment.

10. The medical device of claim 1, wherein the first and second leaflets comprise a natural material.

11. The medical device of claim 10, wherein the natural material comprises a bioremodelable material.

12. The medical device of claim 11, wherein the bioremodelable material comprises an extracellular matrix material.

13. The medical device of claim 12, wherein the extracellular matrix material comprises small intestine submucosa.

14. The medical device of claim 12, wherein the extracellular matrix material is selected from the group consisting of stomach submucosa, liver basement membrane, urinary bladder submucosa, tissue mucosa, and dura mater.

15. The medical device of claim 10, wherein the natural material comprises lung ligament.

16. The medical device of claim 10, wherein the natural material comprises visceral pleura.

17. The medical device of claim 10, wherein the natural material comprises fixed tissue.

18. A medical device for regulating fluid flow through a body vessel of a patient, comprising:

an expandable support frame having a longitudinal axis, an outer circumference, and an unexpanded configuration, the support frame comprising:

a first connector segment having an axial length and comprising substantially parallel first and second struts and a first connecting bar extending between and joining the first and second struts on a first transverse axis that orthogonally intersects the first connector segment at a point that is about $\frac{1}{4}^{th}$ the axial length of the first connector segment;

a second connector segment having an axial length and disposed substantially opposite the first connector segment with respect to said longitudinal axis, the second connector segment comprising substantially parallel third and fourth struts and a second connecting bar extending between and joining the third and fourth struts on a second transverse axis that orthogonally intersects the second connector segment at a point that is about $\frac{1}{4}^{th}$ the axial length of the second connector segment;

a third connector segment disposed circumferentially adjacent the first and second connector segments;

a fourth connector segment disposed substantially opposite the third connector segment with respect to said longitudinal axis;

a proximal portion defining a first circumferential serpentine path joined to the first, second, third, and fourth connector segments; and a distal portion defining a second circumferential serpentine path joined to the first, second, third, and fourth connector segments and comprising a first connector strut extending between and joining the first and third connector segments, a second connector strut extending between and joining the second and third connector segments, a third connector strut extending between and joining the first and fourth connector segments, and a fourth connector strut extending between and joining the second and fourth connector segments, each of the first connector strut, the second connector strut, the third connector strut, and the fourth connector strut comprising a curvilinear strut that includes a straight portion;

a first leaflet attached to the support frame along an attachment pathway extending along the first and second connector struts and only along a first portion of the first connector segment extending from the distal portion and toward the proximal portion to the first connecting bar and a first portion of the second connector segment extending from the distal portion and toward the proximal portion to the second connecting bar, the first leaflet having a first free edge and a first inner surface; and a second leaflet attached to the support frame along a second attachment pathway extending along the third and fourth connector struts and along a second portion of the first connector segment to the first connecting bar and a second portion of the second connector segment to the second connecting bar, the second leaflet having a second free edge and a second inner surface;

wherein the first and second free edges cooperatively define a valve orifice;

wherein the first portion of the first connector segment is about $\frac{1}{4}^{th}$ the axial length of the first connector segment; and wherein the first portion of the second connector segment is about $\frac{1}{4}^{th}$ the axial length of the second connector segment.

19. The medical device of claim 18, wherein the third connector segment is only a single strut extending from the proximal portion to the first connector strut and the second connector strut.

20. A medical device for regulating fluid flow through a body vessel of a patient, comprising:

an expandable support frame having a longitudinal axis, an outer circumference, and an unexpanded configuration, the support frame comprising:

a first connector segment having an axial length and comprising substantially parallel first and second struts and a first connecting bar extending between and joining the first and second struts on a first transverse axis that orthogonally intersects the first connector segment at a point that is about $¼^{th}$ the axial length of the first connector segment;

a second connector segment having an axial length and disposed substantially opposite the first connector segment with respect to said longitudinal axis, the second connector segment comprising substantially parallel third and fourth struts and a second connecting bar extending between and joining the third and fourth struts on a second transverse axis that orthogonally intersects the second connector segment at a point that is about $¼^{th}$ the axial length of the second connector segment;

a third connector segment disposed circumferentially adjacent the first and second connector segments;

a fourth connector segment disposed substantially opposite the third connector segment with respect to said longitudinal axis;

a proximal portion defining a first circumferential serpentine path joined to the first, second, third, and fourth connector segments; and a distal portion defining a second circumferential serpentine path joined to the first, second, third, and fourth connector segments and comprising a first connector strut extending between and joining the first and third connector segments, a second connector strut extending between and joining the second and third connector segments, a third connector strut extending between and joining the first and fourth connector segments, and a fourth connector strut extending between and joining the second and fourth connector segments, each of the first connector strut, the second connector strut, the third connector strut, and the fourth connector strut comprising a curvilinear strut that includes a straight portion;

a first leaflet attached to the support frame along an attachment pathway extending along the first and second connector struts and only along a first portion of the first connector segment extending from the distal portion and toward the proximal portion to the first connecting bar and a first portion of the second connector segment extending from the distal portion and toward the proximal portion to the second connecting bar, the first leaflet comprising fixed natural tissue comprising visceral pleura and having a first free edge and a first inner surface; and a second leaflet attached to the support frame along a second attachment pathway extending along the third and fourth connector struts and along a second portion of the first connector segment to the first connecting bar and a second portion of the second connector segment to the second connecting bar, the second leaflet comprising fixed natural tissue comprising visceral pleura and having a second free edge and a second inner surface;

wherein the first and second free edges cooperatively define a valve orifice;

wherein the first portion of the first connector segment is about $¼^{th}$ the axial length of the first connector segment; and wherein the first portion of the second connector segment is about $¼^{th}$ the axial length of the second connector segment.

* * * * *